US008638200B2

(12) United States Patent
Milne et al.

(10) Patent No.: US 8,638,200 B2
(45) Date of Patent: *Jan. 28, 2014

(54) VENTILATOR-INITIATED PROMPT REGARDING AUTO-PEEP DETECTION DURING VOLUME VENTILATION OF NON-TRIGGERING PATIENT

(75) Inventors: Gary Milne, Louisville, CO (US); Kirk Hensley, Dublin, OH (US); Peter R. Doyle, Vista, CA (US); Gardner Kimm, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 374 days.

This patent is subject to a terminal disclaimer.

(21) Appl. No.: 12/775,565

(22) Filed: May 7, 2010

(65) Prior Publication Data

US 2011/0273299 A1 Nov. 10, 2011

(51) Int. Cl.
*G08B 5/22* (2006.01)
(52) U.S. Cl.
USPC ............ 340/286.07; 128/204.18; 128/204.21; 128/204.23; 340/539.12; 340/573.1; 600/323; 600/529
(58) Field of Classification Search
USPC ........ 340/539.12, 286.07; 600/323, 529, 554, 600/546, 547, 587, 534; 128/204.21, 128/204.18, 204.23, 925; 702/19; 715/808
See application file for complete search history.

(56) References Cited

U.S. PATENT DOCUMENTS

| | | | |
|---|---|---|---|
| 4,546,770 A * | 10/1985 | Schlessinger et al. ........ 600/301 |
| 4,752,089 A | 6/1988 | Carter | |
| 4,917,080 A | 4/1990 | Bayerlein | |
| 4,921,642 A | 5/1990 | LaTorraca | |
| 4,954,799 A | 9/1990 | Kumar | |
| 5,057,822 A | 10/1991 | Hoffman | |
| 5,072,737 A | 12/1991 | Goulding | |
| 5,150,291 A | 9/1992 | Cummings et al. | |
| 5,161,525 A | 11/1992 | Kimm et al. | |
| 5,237,987 A | 8/1993 | Anderson et al. | |

(Continued)

FOREIGN PATENT DOCUMENTS

| WO | WO 95/16484 | 6/1995 |
|---|---|---|
| WO | WO9829790 | 7/1998 |

(Continued)

OTHER PUBLICATIONS

Puritan Bennett 840 Ventilator System SMARTER Breath Delivery information sheet by tyco Healthcare, undated, 1 page.

(Continued)

*Primary Examiner* — Brent Swarthout

(57) ABSTRACT

This disclosure describes systems and methods for monitoring and evaluating ventilatory parameters, analyzing those parameters and providing useful notifications and recommendations to clinicians. That is, modern ventilators monitor, evaluate, and graphically represent a myriad of ventilatory parameters. However, many clinicians may not easily identify or recognize data patterns and correlations indicative of certain patient conditions, changes in patient condition, and/or effectiveness of ventilatory treatment. Further, clinicians may not readily determine appropriate ventilatory adjustments that may address certain patient conditions and/or the effectiveness of ventilatory treatment. Specifically, clinicians may not readily detect or recognize the presence of Auto-PEEP during volume ventilation of a non-triggering patient. According to embodiments, a ventilator may be configured to monitor and evaluate diverse ventilatory parameters to detect Auto-PEEP and may issue suitable notifications and recommendations to the clinician when Auto-PEEP is implicated. The suitable notifications and recommendations may further be provided in a hierarchical format.

18 Claims, 6 Drawing Sheets

(56) References Cited

U.S. PATENT DOCUMENTS

| | | |
|---|---|---|
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,319,540 A | 6/1994 | Isaza et al. |
| 5,325,861 A | 7/1994 | Goulding |
| 5,333,606 A | 8/1994 | Schneider et al. |
| 5,335,654 A | 8/1994 | Rapoport |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,438,980 A | 8/1995 | Phillips |
| 5,443,075 A | 8/1995 | Holscher |
| 5,490,502 A | 2/1996 | Rapoport et al. |
| 5,513,631 A | 5/1996 | McWilliams |
| 5,517,983 A | 5/1996 | Deighan et al. |
| 5,520,071 A | 5/1996 | Jones |
| 5,520,192 A | 5/1996 | Kitney et al. |
| 5,524,615 A | 6/1996 | Power |
| 5,531,221 A | 7/1996 | Power |
| 5,542,415 A | 8/1996 | Brady |
| 5,544,674 A | 8/1996 | Kelly |
| 5,549,106 A | 8/1996 | Gruenke et al. |
| 5,596,984 A | 1/1997 | O'Mahony et al. |
| 5,598,838 A | 2/1997 | Servidio et al. |
| 5,605,151 A | 2/1997 | Lynn |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,678,539 A | 10/1997 | Schubert et al. |
| 5,715,415 A | 2/1998 | Dazey et al. |
| 5,715,812 A | 2/1998 | Deighan et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,803,066 A | 9/1998 | Rapoport et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,891,023 A | 4/1999 | Lynn |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,927,274 A | 7/1999 | Servidio et al. |
| 5,931,160 A | 8/1999 | Gilmore et al. |
| 5,934,274 A | 8/1999 | Merrick et al. |
| 5,957,129 A | 9/1999 | Tham et al. |
| 5,964,220 A | 10/1999 | Boussignac et al. |
| 6,024,089 A | 2/2000 | Wallace et al. |
| 6,041,780 A | 3/2000 | Richard et al. |
| 6,047,860 A | 4/2000 | Sanders |
| 6,067,022 A | 5/2000 | Laswick et al. |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony et al. |
| 6,148,814 A | 11/2000 | Clemmer et al. |
| 6,158,430 A | 12/2000 | Pfeiffer et al. |
| 6,158,432 A | 12/2000 | Biondi et al. |
| 6,161,539 A | 12/2000 | Winter |
| 6,192,876 B1 | 2/2001 | Denyer et al. |
| 6,206,001 B1 | 3/2001 | Garber et al. |
| 6,206,837 B1 | 3/2001 | Brugnoli |
| 6,220,245 B1 | 4/2001 | Takabayashi et al. |
| 6,223,064 B1 | 4/2001 | Lynn et al. |
| 6,240,920 B1 * | 6/2001 | Strom ............... 128/204.23 |
| 6,269,812 B1 | 8/2001 | Wallace et al. |
| 6,273,444 B1 | 8/2001 | Power |
| 6,283,119 B1 | 9/2001 | Bourdon |
| 6,305,372 B1 | 10/2001 | Servidio |
| 6,305,373 B1 | 10/2001 | Wallace et al. |
| 6,321,748 B1 | 11/2001 | O'Mahoney |
| 6,322,502 B1 | 11/2001 | Schoenberg et al. |
| 6,325,785 B1 | 12/2001 | Babkes et al. |
| 6,342,039 B1 | 1/2002 | Lynn et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,398,728 B1 | 6/2002 | Bardy |
| 6,412,483 B1 | 7/2002 | Jones et al. |
| 6,439,229 B1 | 8/2002 | Du et al. |
| 6,463,930 B2 | 10/2002 | Biondi et al. |
| 6,467,478 B1 | 10/2002 | Merrick et al. |
| 6,546,930 B1 | 4/2003 | Emerson et al. |
| 6,551,243 B2 | 4/2003 | Bocionek et al. |
| 6,553,991 B1 | 4/2003 | Isaza |
| 6,557,553 B1 | 5/2003 | Borrello |
| 6,564,797 B1 | 5/2003 | Mechlenburg et al. |
| 6,569,095 B2 | 5/2003 | Eggers |
| 6,571,795 B2 | 6/2003 | Bourdon |
| 6,578,575 B1 * | 6/2003 | Jonson ............... 128/204.21 |
| 6,584,973 B1 | 7/2003 | Biondi et al. |
| 6,609,016 B1 | 8/2003 | Lynn |
| 6,622,726 B1 | 9/2003 | Du |
| 6,644,310 B1 | 11/2003 | Delache et al. |
| 6,644,312 B2 | 11/2003 | Berthon-Jones et al. |
| 6,668,824 B1 | 12/2003 | Isaza et al. |
| 6,668,829 B2 | 12/2003 | Biondi et al. |
| 6,675,801 B2 | 1/2004 | Wallace et al. |
| 6,709,405 B2 | 3/2004 | Jonson |
| 6,717,589 B1 | 4/2004 | Grillo et al. |
| 6,718,974 B1 | 4/2004 | Moberg |
| 6,718,975 B2 | 4/2004 | Blomberg |
| 6,725,447 B1 | 4/2004 | Gilman et al. |
| 6,739,337 B2 | 5/2004 | Isaza |
| 6,743,172 B1 | 6/2004 | Blike |
| 6,745,764 B2 | 6/2004 | Hickle |
| 6,748,252 B2 | 6/2004 | Lynn et al. |
| 6,752,150 B1 | 6/2004 | Remmers et al. |
| 6,760,608 B2 | 7/2004 | Lynn |
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,804,656 B1 | 10/2004 | Rosenfeld et al. |
| 6,807,965 B1 | 10/2004 | Hickle |
| 6,814,074 B1 | 11/2004 | Nadjafizadeh et al. |
| 6,832,609 B2 | 12/2004 | Wright et al. |
| 6,845,773 B2 | 1/2005 | Berthon-Jones et al. |
| 6,860,266 B2 | 3/2005 | Blike |
| 6,866,040 B1 | 3/2005 | Bourdon |
| 6,949,073 B2 | 9/2005 | Sarel |
| 6,960,854 B2 | 11/2005 | Nadjafizadeh et al. |
| 6,986,347 B2 | 1/2006 | Hickle |

| | | |
|---|---|---|
| 7,017,574 B2 | 3/2006 | Biondi et al. |
| 7,018,341 B2 | 3/2006 | Wright et al. |
| 7,036,504 B2 | 5/2006 | Wallace et al. |
| 7,046,254 B2 | 5/2006 | Brown et al. |
| 7,051,735 B2 | 5/2006 | Mechlenburg et al. |
| 7,066,173 B2 | 6/2006 | Banner et al. |
| 7,073,501 B2 | 7/2006 | Remmers et al. |
| 7,077,131 B2 | 7/2006 | Hansen |
| 7,081,091 B2 | 7/2006 | Merrett et al. |
| 7,081,095 B2 | 7/2006 | Lynn et al. |
| RE39,225 E | 8/2006 | Isaza et al. |
| 7,086,399 B2 | 8/2006 | Makinson et al. |
| 7,089,937 B2 | 8/2006 | Berthon-Jones et al. |
| 7,117,438 B2 | 10/2006 | Wallace et al. |
| 7,201,734 B2 | 4/2007 | Hickle |
| 7,207,945 B2 | 4/2007 | Bardy |
| 7,210,478 B2 | 5/2007 | Banner et al. |
| 7,222,623 B2 | 5/2007 | DeVries et al. |
| 7,247,154 B2 | 7/2007 | Hickle |
| 7,256,708 B2 | 8/2007 | Rosenfeld et al. |
| 7,258,670 B2 | 8/2007 | Bardy |
| 7,270,126 B2 | 9/2007 | Wallace et al. |
| 7,307,543 B2 | 12/2007 | Rosenfeld et al. |
| 7,308,894 B2 | 12/2007 | Hickle |
| 7,315,825 B2 | 1/2008 | Rosenfeld et al. |
| 7,321,862 B2 | 1/2008 | Rosenfeld et al. |
| 7,322,937 B2 | 1/2008 | Blomberg et al. |
| 7,334,578 B2 | 2/2008 | Biondi et al. |
| 7,346,846 B2 | 3/2008 | Rossi, Jr. et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,395,216 B2 | 7/2008 | Rosenfeld et al. |
| 7,398,115 B2 | 7/2008 | Lynn |
| 7,428,902 B2 | 9/2008 | Du et al. |
| 7,433,827 B2 | 10/2008 | Rosenfeld et al. |
| 7,454,359 B2 | 11/2008 | Rosenfeld et al. |
| 7,454,360 B2 | 11/2008 | Rosenfeld et al. |
| 7,460,959 B2 | 12/2008 | Jafari |
| 7,467,094 B2 | 12/2008 | Rosenfeld et al. |
| 7,475,019 B2 | 1/2009 | Rosenfeld et al. |
| 7,487,773 B2 | 2/2009 | Li |
| 7,520,279 B2 | 4/2009 | Berthon-Jones |
| 7,556,038 B2 | 7/2009 | Kirby et al. |
| 7,561,912 B2 | 7/2009 | Schatz et al. |
| 7,562,657 B2 * | 7/2009 | Blanch et al. ............ 128/204.23 |
| 7,565,905 B2 | 7/2009 | Hickle |
| 7,650,291 B2 | 1/2010 | Rosenfeld et al. |
| 7,654,802 B2 | 2/2010 | Crawford, Jr. et al. |
| 7,681,571 B2 | 3/2010 | Makinson et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,778,851 B2 | 8/2010 | Schoenberg et al. |
| 7,784,461 B2 | 8/2010 | Figueiredo et al. |
| 7,802,571 B2 * | 9/2010 | Tehrani .................... 128/204.23 |
| 7,823,588 B2 | 11/2010 | Hansen |
| 7,831,450 B2 | 11/2010 | Schoenberg et al. |
| 7,855,716 B2 | 12/2010 | McCreary et al. |
| D632,796 S | 2/2011 | Ross et al. |
| D632,797 S | 2/2011 | Ross et al. |
| 7,886,231 B2 | 2/2011 | Hopermann |
| 7,886,739 B2 * | 2/2011 | Soliman et al. .......... 128/204.21 |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,224,636 B2 | 7/2012 | Kundert |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0004893 A1 | 6/2001 | Biondi et al. |
| 2001/0027791 A1 | 10/2001 | Wallace et al. |
| 2002/0023644 A1 | 2/2002 | Berthon-Jones |
| 2002/0026941 A1 | 3/2002 | Biondi et al. |
| 2002/0117173 A1 | 8/2002 | Lynn et al. |
| 2002/0177758 A1 | 11/2002 | Schoenberg et al. |
| 2003/0036687 A1 | 2/2003 | Schoenberg et al. |
| 2003/0106553 A1 | 6/2003 | Vanderveen |
| 2003/0121519 A1 | 7/2003 | Estes et al. |
| 2003/0140928 A1 | 7/2003 | Bui et al. |
| 2003/0141981 A1 | 7/2003 | Bui et al. |
| 2003/0153818 A1 | 8/2003 | Bocionek et al. |
| 2003/0158466 A1 | 8/2003 | Lynn et al. |
| 2003/0188748 A1 | 10/2003 | Sinderby et al. |
| 2003/0230308 A1 | 12/2003 | Linden |
| 2004/0041828 A1 | 3/2004 | Zellhoefer |
| 2004/0121767 A1 | 6/2004 | Simpson et al. |
| 2004/0167804 A1 | 8/2004 | Simpson et al. |
| 2004/0172302 A1 | 9/2004 | Martucci et al. |
| 2004/0236240 A1 | 11/2004 | Kraus et al. |
| 2004/0244807 A1 | 12/2004 | Jiangno et al. |
| 2005/0016534 A1 | 1/2005 | Ost |
| 2005/0039127 A1 | 2/2005 | Davis |
| 2005/0039748 A1 | 2/2005 | Andrieux |
| 2005/0043969 A1 | 2/2005 | Sarel |
| 2005/0055242 A1 | 3/2005 | Bello et al. |
| 2005/0065817 A1 | 3/2005 | Mihai et al. |
| 2005/0112325 A1 | 5/2005 | Hickle |
| 2005/0124866 A1 | 6/2005 | Elaz et al. |
| 2005/0133024 A1 | 6/2005 | Coifman |
| 2005/0139212 A1 | 6/2005 | Bourdon |
| 2005/0188991 A1 | 9/2005 | Sun et al. |
| 2005/0204310 A1 | 9/2005 | De Zwart et al. |
| 2006/0085229 A9 | 4/2006 | Rosenfeld et al. |
| 2006/0089543 A1 | 4/2006 | Youn-ho et al. |
| 2006/0112959 A1 | 6/2006 | Mechlenburg et al. |
| 2006/0122869 A9 | 6/2006 | Rosenfeld et al. |
| 2006/0135878 A1 | 6/2006 | Wright et al. |
| 2006/0144144 A1 | 7/2006 | Seto |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0161459 A9 | 7/2006 | Rosenfeld et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0201506 A1 | 9/2006 | Makinson et al. |
| 2006/0235324 A1 | 10/2006 | Lynn |
| 2006/0237015 A1 | 10/2006 | Berthon-Jones et al. |
| 2006/0249149 A1 | 11/2006 | Meier et al. |
| 2006/0249151 A1 | 11/2006 | Gambone |
| 2006/0271409 A1 | 11/2006 | Rosenfeld et al. |
| 2006/0276701 A1 | 12/2006 | Ray |
| 2006/0294464 A1 | 12/2006 | Tokimoto et al. |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0050715 A1 | 3/2007 | Behar |
| 2007/0077200 A1 | 4/2007 | Baker |
| 2007/0093721 A1 | 4/2007 | Lynn et al. |
| 2007/0129647 A1 | 6/2007 | Lynn |
| 2007/0149860 A1 | 6/2007 | Lynn et al. |
| 2007/0163579 A1 | 7/2007 | Li et al. |
| 2007/0173702 A1 | 7/2007 | Dlugos et al. |

| | | | |
|---|---|---|---|
| 2007/0191688 A1 | 8/2007 | Lynn | |
| 2007/0191697 A1 | 8/2007 | Lynn et al. | |
| 2007/0199566 A1 | 8/2007 | Be'eri | |
| 2007/0203415 A1 | 8/2007 | Bardy | |
| 2007/0203422 A1 | 8/2007 | Bardy | |
| 2007/0203423 A1 | 8/2007 | Bardy | |
| 2007/0213658 A1 | 9/2007 | Hickle | |
| 2007/0227537 A1 | 10/2007 | Bemister et al. | |
| 2007/0232867 A1 | 10/2007 | Hansmann | |
| 2007/0284361 A1 | 12/2007 | Nadjafizadeh et al. | |
| 2008/0000479 A1 | 1/2008 | Elaz et al. | |
| 2008/0021379 A1 | 1/2008 | Hickle | |
| 2008/0041380 A1 | 2/2008 | Wallace et al. | |
| 2008/0053441 A1 | 3/2008 | Gottlib et al. | |
| 2008/0066752 A1 | 3/2008 | Baker et al. | |
| 2008/0072896 A1 | 3/2008 | Setzer et al. | |
| 2008/0072900 A1 | 3/2008 | Kenyon et al. | |
| 2008/0072902 A1 | 3/2008 | Setzer et al. | |
| 2008/0078390 A1 | 4/2008 | Milne et al. | |
| 2008/0081974 A1 | 4/2008 | Pav | |
| 2008/0083644 A1 | 4/2008 | Janbakhsh et al. | |
| 2008/0086691 A1 | 4/2008 | Hopermann | |
| 2008/0091117 A1 | 4/2008 | Choncholas et al. | |
| 2008/0092043 A1 | 4/2008 | Trethewey | |
| 2008/0092894 A1 | 4/2008 | Nicolazzi et al. | |
| 2008/0097234 A1 | 4/2008 | Nicolazzi et al. | |
| 2008/0200775 A1 | 8/2008 | Lynn | |
| 2008/0200819 A1 | 8/2008 | Lynn et al. | |
| 2008/0236582 A1 | 10/2008 | Tehrani | |
| 2008/0314385 A1 | 12/2008 | Brunner et al. | |
| 2009/0020120 A1 | 1/2009 | Schatzl et al. | |
| 2009/0143694 A1 | 6/2009 | Krauss et al. | |
| 2009/0149723 A1 | 6/2009 | Krauss et al. | |
| 2009/0165795 A1 | 7/2009 | Nadjafizadeh et al. | |
| 2009/0171176 A1 | 7/2009 | Andersohn | |
| 2009/0171226 A1 | 7/2009 | Campbell et al. | |
| 2009/0205661 A1 | 8/2009 | Stephenson et al. | |
| 2009/0205663 A1 | 8/2009 | Vandine et al. | |
| 2009/0241952 A1 | 10/2009 | Nicolazzi et al. | |
| 2009/0241953 A1 | 10/2009 | Vandine et al. | |
| 2009/0241956 A1 | 10/2009 | Baker, Jr. et al. | |
| 2009/0241957 A1 | 10/2009 | Baker, Jr. | |
| 2009/0241958 A1 | 10/2009 | Baker, Jr. | |
| 2009/0241962 A1 | 10/2009 | Jafari et al. | |
| 2009/0247891 A1 | 10/2009 | Wood | |
| 2009/0270752 A1 | 10/2009 | Coifman | |
| 2009/0275811 A1 | 11/2009 | Schatz et al. | |
| 2009/0293877 A1 | 12/2009 | Blanch et al. | |
| 2009/0301486 A1 | 12/2009 | Masic | |
| 2009/0301487 A1 | 12/2009 | Masic | |
| 2009/0301490 A1 | 12/2009 | Masic | |
| 2009/0301491 A1 | 12/2009 | Masic et al. | |
| 2009/0314290 A1 | 12/2009 | Hickle | |
| 2010/0011307 A1 | 1/2010 | Desfossez et al. | |
| 2010/0024820 A1 | 2/2010 | Bourdon | |
| 2010/0030091 A1 | 2/2010 | Fine | |
| 2010/0037895 A1 | 2/2010 | Berthon-Jones et al. | |
| 2010/0051026 A1 | 3/2010 | Graboi | |
| 2010/0051029 A1 | 3/2010 | Jafari et al. | |
| 2010/0069761 A1 | 3/2010 | Karst et al. | |
| 2010/0071689 A1 | 3/2010 | Thiessen | |
| 2010/0071692 A1 | 3/2010 | Porges | |
| 2010/0071695 A1 | 3/2010 | Thiessen | |
| 2010/0071696 A1 | 3/2010 | Jafari | |
| 2010/0071697 A1 | 3/2010 | Jafari et al. | |
| 2010/0078017 A1 | 4/2010 | Andrieux et al. | |
| 2010/0078026 A1 | 4/2010 | Andrieux et al. | |
| 2010/0081119 A1 | 4/2010 | Jafari et al. | |
| 2010/0081955 A1 | 4/2010 | Wood, Jr. et al. | |
| 2010/0108064 A1 | 5/2010 | Blackwell et al. | |
| 2010/0139660 A1 | 6/2010 | Adahan | |
| 2010/0147303 A1 | 6/2010 | Jafari et al. | |
| 2010/0186744 A1 | 7/2010 | Andrieux | |
| 2010/0192094 A1 | 7/2010 | Jeha et al. | |
| 2010/0199015 A1 | 8/2010 | Martucci et al. | |
| 2010/0218765 A1 | 9/2010 | Jafari et al. | |
| 2010/0218766 A1 | 9/2010 | Milne | |
| 2010/0218767 A1 | 9/2010 | Jafari et al. | |
| 2010/0236555 A1 | 9/2010 | Jafari et al. | |
| 2010/0242961 A1 | 9/2010 | Mougel et al. | |
| 2010/0282259 A1 | 11/2010 | Figueiredo et al. | |
| 2010/0288283 A1 | 11/2010 | Campbell et al. | |
| 2010/0292544 A1 | 11/2010 | Sherman et al. | |
| 2010/0300446 A1 | 12/2010 | Nicolazzi et al. | |
| 2011/0004489 A1 | 1/2011 | Schoenberg et al. | |
| 2011/0011400 A1 | 1/2011 | Gentner et al. | |
| 2011/0023878 A1 | 2/2011 | Thiessen | |
| 2011/0023879 A1 | 2/2011 | Vandine et al. | |
| 2011/0023880 A1 | 2/2011 | Thiessen | |
| 2011/0023881 A1 | 2/2011 | Thiessen | |
| 2011/0029910 A1 | 2/2011 | Thiessen | |
| 2011/0041849 A1 | 2/2011 | Chen et al. | |
| 2011/0041850 A1 | 2/2011 | Vandine et al. | |
| 2011/0126829 A1 | 6/2011 | Carter et al. | |
| 2011/0126832 A1 | 6/2011 | Winter et al. | |
| 2011/0126834 A1 | 6/2011 | Winter et al. | |
| 2011/0126835 A1 | 6/2011 | Winter et al. | |
| 2011/0126836 A1 | 6/2011 | Winter et al. | |
| 2011/0126837 A1 | 6/2011 | Winter et al. | |
| 2011/0128008 A1 | 6/2011 | Carter | |
| 2011/0132361 A1 | 6/2011 | Sanchez | |
| 2011/0132362 A1 | 6/2011 | Sanchez | |
| 2011/0132364 A1 | 6/2011 | Ogilvie et al. | |
| 2011/0132365 A1 | 6/2011 | Patel et al. | |
| 2011/0132366 A1 | 6/2011 | Ogilvie et al. | |
| 2011/0132367 A1 | 6/2011 | Patel | |
| 2011/0132368 A1 | 6/2011 | Sanchez et al. | |
| 2011/0132369 A1 | 6/2011 | Sanchez | |
| 2011/0132371 A1 | 6/2011 | Sanchez et al. | |
| 2011/0133936 A1 | 6/2011 | Sanchez et al. | |
| 2011/0138308 A1 | 6/2011 | Palmer et al. | |
| 2011/0138309 A1 | 6/2011 | Skidmore et al. | |
| 2011/0138311 A1 | 6/2011 | Palmer | |
| 2011/0138315 A1 | 6/2011 | Vandine et al. | |
| 2011/0138323 A1 | 6/2011 | Skidmore et al. | |
| 2011/0146681 A1 | 6/2011 | Jafari et al. | |
| 2011/0146683 A1 | 6/2011 | Jafari et al. | |
| 2011/0154241 A1 | 6/2011 | Skidmore et al. | |
| 2011/0168177 A1 | 7/2011 | Connor | |
| 2011/0175728 A1 | 7/2011 | Baker, Jr. | |
| 2011/0196251 A1 | 8/2011 | Jourdain et al. | |
| 2011/0209702 A1 | 9/2011 | Vuong et al. | |
| 2011/0209704 A1 | 9/2011 | Jafari et al. | |
| 2011/0209707 A1 | 9/2011 | Terhark | |
| 2011/0213215 A1 | 9/2011 | Doyle et al. | |
| 2011/0230780 A1 | 9/2011 | Sanborn et al. | |
| 2011/0249006 A1 | 10/2011 | Wallace et al. | |
| 2011/0259330 A1 | 10/2011 | Jafari et al. | |
| 2011/0259332 A1 | 10/2011 | Sanchez et al. | |
| 2011/0259333 A1 | 10/2011 | Sanchez et al. | |
| 2011/0265024 A1 | 10/2011 | Leone et al. | |
| 2011/0271960 A1 | 11/2011 | Milne et al. | |
| 2012/0000467 A1 | 1/2012 | Milne et al. | |
| 2012/0000468 A1 | 1/2012 | Milne et al. | |
| 2012/0000469 A1 | 1/2012 | Milne et al. | |
| 2012/0000470 A1 | 1/2012 | Milne et al. | |
| 2012/0029317 A1 | 2/2012 | Doyle et al. | |
| 2012/0030611 A1 | 2/2012 | Skidmore | |
| 2012/0060841 A1 | 3/2012 | Crawford, Jr. et al. | |
| 2012/0071729 A1 | 3/2012 | Doyle et al. | |
| 2012/0090611 A1 | 4/2012 | Graboi et al. | |
| 2012/0096381 A1 | 4/2012 | Milne et al. | |
| 2012/0133519 A1 | 5/2012 | Milne et al. | |
| 2012/0136222 A1 | 5/2012 | Doyle et al. | |
| 2012/0137249 A1 | 5/2012 | Milne et al. | |
| 2012/0137250 A1 | 5/2012 | Milne et al. | |
| 2012/0167885 A1 | 7/2012 | Masic et al. | |
| 2012/0185792 A1 | 7/2012 | Kimm et al. | |
| 2012/0197578 A1 | 8/2012 | Vig et al. | |
| 2012/0197580 A1 | 8/2012 | Vij et al. | |
| 2012/0211008 A1 | 8/2012 | Perine et al. | |
| 2012/0216809 A1 | 8/2012 | Milne et al. | |
| 2012/0216810 A1 | 8/2012 | Jafari et al. | |
| 2012/0216811 A1 | 8/2012 | Kimm et al. | |
| 2012/0226444 A1 | 9/2012 | Milne et al. | |
| 2012/0247471 A1 | 10/2012 | Masic et al. | |

FOREIGN PATENT DOCUMENTS

| | | |
|---|---|---|
| WO | WO 98/41267 | 9/1998 |
| WO | WO 98/41269 | 9/1998 |
| WO | WO 98/41270 | 9/1998 |
| WO | WO 98/41271 | 9/1998 |
| WO | WO9853732 | 12/1998 |
| WO | WO 99/62403 | 12/1999 |
| WO | WO 00/45882 | 8/2000 |
| WO | WO0079466 | 12/2000 |
| WO | WO 01/00264 | 1/2001 |
| WO | WO 01/00265 | 1/2001 |
| WO | WO 02/45566 | 6/2002 |
| WO | WO 02/095200 | 11/2002 |
| WO | WO 03/053503 | 7/2003 |
| WO | WO 03/102850 | 12/2003 |
| WO | WO 2004/030509 | 4/2004 |
| WO | WO 2004/069095 | 8/2004 |
| WO | WO 2004/070546 | 8/2004 |
| WO | WO 2004/070548 | 8/2004 |
| WO | WO 2004/070549 | 8/2004 |
| WO | WO 2004/070556 | 8/2004 |
| WO | WO 2004/070557 | 8/2004 |
| WO | WO 2004/070562 | 8/2004 |
| WO | WO 2004/070994 | 8/2004 |
| WO | WO 2004/070995 | 8/2004 |
| WO | WO 2004/082751 | 9/2004 |
| WO | WO 2005/050525 | 6/2005 |
| WO | WO 2005/051177 | 6/2005 |
| WO | WO 2006/012205 | 2/2006 |
| WO | WO 2007/050435 | 5/2007 |
| WO | WO 2007/085110 | 8/2007 |
| WO | WO2007145948 | 12/2007 |
| WO | WO 2008/021222 | 2/2008 |
| WO | WO 2010/011928 | 1/2010 |

OTHER PUBLICATIONS

Tobin, M. "Principles and Practices of Mechanical Ventilation," Second Ed. McGraw Hill 2006. p. 1062.
Thille, A., et al. "Patient-Ventilator Asynchrony During Assisted Mechanical Ventilation," Intensive Care Med. (2006) 32:1515-1522.
The ARDSNET. "Ventilation with Lower Tidal Volumes as Compared with Traditional Tidal Volumes for Acute Lung Injury and the Acute Respiratory Distress Syndrome," New England Journal of Medicine, vol. 342 No. 18, May 4, 2000, pp. 1301-1308.
7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1988, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Egan's Fundamentals of Respiratory Care (2003) $8^{th}$ Edition, Editors Robert L. Wilkins, James K. Stoller and Craig L. Scanlan, p. 996.
Mechanical Ventilation: Physiological and Clinical Applications (2006) $4^{th}$ Edition, Editors Susan P. Pilbeam and J.M. Cairo, pp. 46-47, 144, 158-160, 168-171, 178-181, 195-202, 222-225, 373-376.
Sassoon, Catherine, MD., "Triggering of the Ventilator In Patient-Ventilator Interactions", Respiratory Care, Jan. 2011, vol. 56, No. 1, pp. 39-51.
U.S. Appl. No. 12/775,550, Office Action mailed Sep. 26, 2012, 32 pgs.
U.S. Appl. No. 12/826,828, Office Action mailed Nov. 2, 2012, 17 pgs.
U.S. Appl. No. 12/826,847, Office Action mailed Nov. 2, 2012, 16 pgs.
U.S. Appl. No. 12/827,075, Office Action mailed Nov. 9, 2012, 16 pgs.
U.S. Appl. No. 12/827,130, Office Action mailed Nov. 9, 2012, 16 pgs.
U.S. Appl. No. 12/775,550, Office Action mailed Feb. 14, 2013, 32 pgs.
U.S. Appl. No. 12/955,523, Office Action mailed Feb. 5, 2013, 8 pgs.
U.S. Appl. No. 12/775,550, Advisory Action mailed Apr. 12, 2013, 3 pgs.
U.S. Appl. No. 12/827,130, Office Action mailed May 8, 2013, 15 pgs.
U.S. Appl. No. 12/827,075, Office Action mailed Apr. 23, 2013, 17 pgs.
U.S. Appl. No. 12/826,847, Office Action mailed Apr. 24, 2013, 14 pgs.
U.S. Appl. No. 12/826,828, Office Action mailed Apr. 24, 2013, 15 pgs.
U.S. Appl. No. 12/955,422, Office Action mailed Apr. 23, 2013, 27 pgs.
U.S. Appl. No. 13/035,974, Office Action mailed Mar. 29, 2013, 14 pgs.
U.S. Appl. No. 12/955,523, Notice of Allowance mailed Jul. 15, 2013, 8 pgs.
U.S. Appl. No. 12/775,550, Office Action mailed Jul. 18, 2013, 37 pgs.
U.S. Appl. No. 12/826,828, Notice of Allowance mailed Aug. 6, 2013, 4 pgs.
U.S. Appl. No. 12/826,847, Notice of Allowance mailed Aug. 5, 2013, 3 pgs.
U.S. Appl. No. 12/827,075, Notice of Allowance mailed Aug. 6, 2013, 3 pgs.
U.S. Appl. No. 12/827,130, Notice of Allowance mailed Aug. 8, 2013, 4 pgs.
U.S. Appl. No. 12/903,358, Office Action mailed Aug. 19, 2013, 15 pgs.
U.S. Appl. No. 12/955,368, Office Action mailed Aug. 2, 2013, 12 pgs.
U.S. Appl. No. 13/035,974, Office Action mailed Sep. 23, 2013, 14 pgs.
U.S. Appl. No. 12/955,422, Notice of Allowance mailed Oct. 8, 2013, 13 pgs.

* cited by examiner

VENTILATOR-INITIATED PROMPT REGARDING AUTO-PEEP DETECTION DURING VOLUME VENTILATION OF NON-TRIGGERING PATIENT

INTRODUCTION

A ventilator is a device that mechanically helps patients breathe by replacing some or all of the muscular effort required to inflate and deflate the lungs. In recent years, there has been an accelerated trend towards an integrated clinical environment. That is, medical devices are becoming increasingly integrated with communication, computing, and control technologies. As a result, modern ventilatory equipment has become increasingly complex, providing for detection and evaluation of a myriad of ventilatoiy parameters. However, due to the shear magnitude of available ventilatory data, many clinicians may not readily assess and evaluate the diverse ventilatory data to detect certain patient conditions and/or changes in patient condition. For example, Auto-PEEP is a dangerous condition associated with gas-trapping in the lungs that may be implicated by slight changes in a variety of different parameters. Although quite serious, Auto-PEEP is difficult to diagnose because it is not easily recognized or detected by clinicians during the ventilation of a patient.

Indeed, clinicians and patients may greatly benefit from ventilator notifications when evaluation of various ventilatory data is indicative of certain patient conditions, changes in patient condition, effectiveness of ventilatory therapy, or otherwise.

Ventilator-Initiated Prompt Regarding Auto-PEEP Detection During Volume Ventilation of Non-Triggering Patient This disclosure describes systems and methods for monitoring and evaluating ventilatory parameters, analyzing ventilatory data associated with those parameters, and providing useful notifications and/or recommendations to clinicians. Modern ventilators monitor, evaluate, and graphically represent a myriad of ventilatory parameters. However, many clinicians may not easily identify or recognize data patterns and correlations indicative of certain patient conditions, changes in patient condition, and/or effectiveness of ventilatory treatment. Further, clinicians may not readily determine appropriate ventilatory adjustments that may address certain patient conditions and/or the effectiveness of ventilatory treatment. Specifically, clinicians may not readily detect or recognize the presence of Auto-PEEP during volume ventilation of a non-triggering patient. According to embodiments, a ventilator may be configured to monitor and evaluate diverse ventilatory parameters to detect Auto-PEEP and may issue suitable notifications and recommendations to the clinician when Auto-PEEP is implicated. The suitable notifications and recommendations may further be provided in a hierarchical format such that the clinician may selectively access summarized and/or detailed information regarding the presence of Auto-PEEP. In more automated systems, recommendations may be automatically implemented.

According to embodiments, a ventilator-implemented method for detecting Auto-PEEP during volume ventilation of a non-triggering patient is provided. The methods include collecting data associated with ventilatory parameters and processing the collected ventilatory parameter data, wherein processing the collected ventilatory parameter data includes deriving ventilatory parameter data from the collected ventilatory parameter data. The methods also include analyzing the processed ventilatory parameter data, which includes receiving one or more predetermined thresholds associated with the processed ventilatory parameter data, and detecting whether the processed ventilatory parameter data breaches the one or more predetermined thresholds. Further, the methods include determining that Auto-PEEP is implicated upon detecting that the processed ventilatory data breaches the one or more predetermined thresholds. The methods further include issuing a smart prompt when Auto-PEEP is implicated.

According to further embodiments, a ventilatory system for issuing a smart prompt when Auto-PEEP is implicated during volume ventilation of a non-triggering patient is provided. Methods implemented by the ventilatory system include detecting that Auto-PEEP is implicated for the non-triggering patient and identifying processed ventilatory parameter data that implicated Auto-PEEP. An appropriate notification message and an appropriate recommendation message may be determined and either or both of the appropriate notification message and the appropriate recommendation message may be displayed.

According to further embodiments, a ventilator graphical user interface for displaying one or more smart prompts corresponding to a detected patient condition is provided. The graphical user interface includes at least one window associated with the graphical user interface and one or more elements within the at least one window comprising at least one smart prompt element for communicating information regarding the detected patient condition.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the claims.

BRIEF DESCRIPTION OF THE DRAWINGS

The following drawing figures, which form a part of this application, are illustrative of described technology and are not meant to limit the scope of the claims in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment for alerting and advising clinicians regarding detected patient conditions.

This disclosure describes systems and methods for monitoring and evaluating ventilatory parameters, analyzing ventilatory data associated with those parameters, and providing useful notifications and/or recommendations to clinicians. Modern ventilators monitor, evaluate, and graphically represent a myriad of ventilatory parameters. However, many clinicians may not easily identify or recognize data patterns and correlations indicative of certain patient conditions, changes in patient condition, and/or effectiveness of ventilatory treatment. Further, clinicians may not readily determine appropriate ventilatory adjustments that may address certain patient conditions and/or the effectiveness of ventilatory treatment. Specifically, clinicians may not readily detect or recognize the presence of Auto-PEEP during volume ventilation of a non-triggering patient. According to embodiments, a ventilator may be configured to monitor and evaluate diverse ventilatory parameters to detect Auto-PEEP and may issue suitable notifications and recommendations to the clinician when Auto-PEEP is implicated. The suitable notifications and recommendations may further be provided in a hierarchical format such that the clinician may selectively access summarized and/or detailed information regarding the presence of Auto-PEEP. In more automated systems, recommendations may be automatically implemented.

Ventilator System

Figure 1:
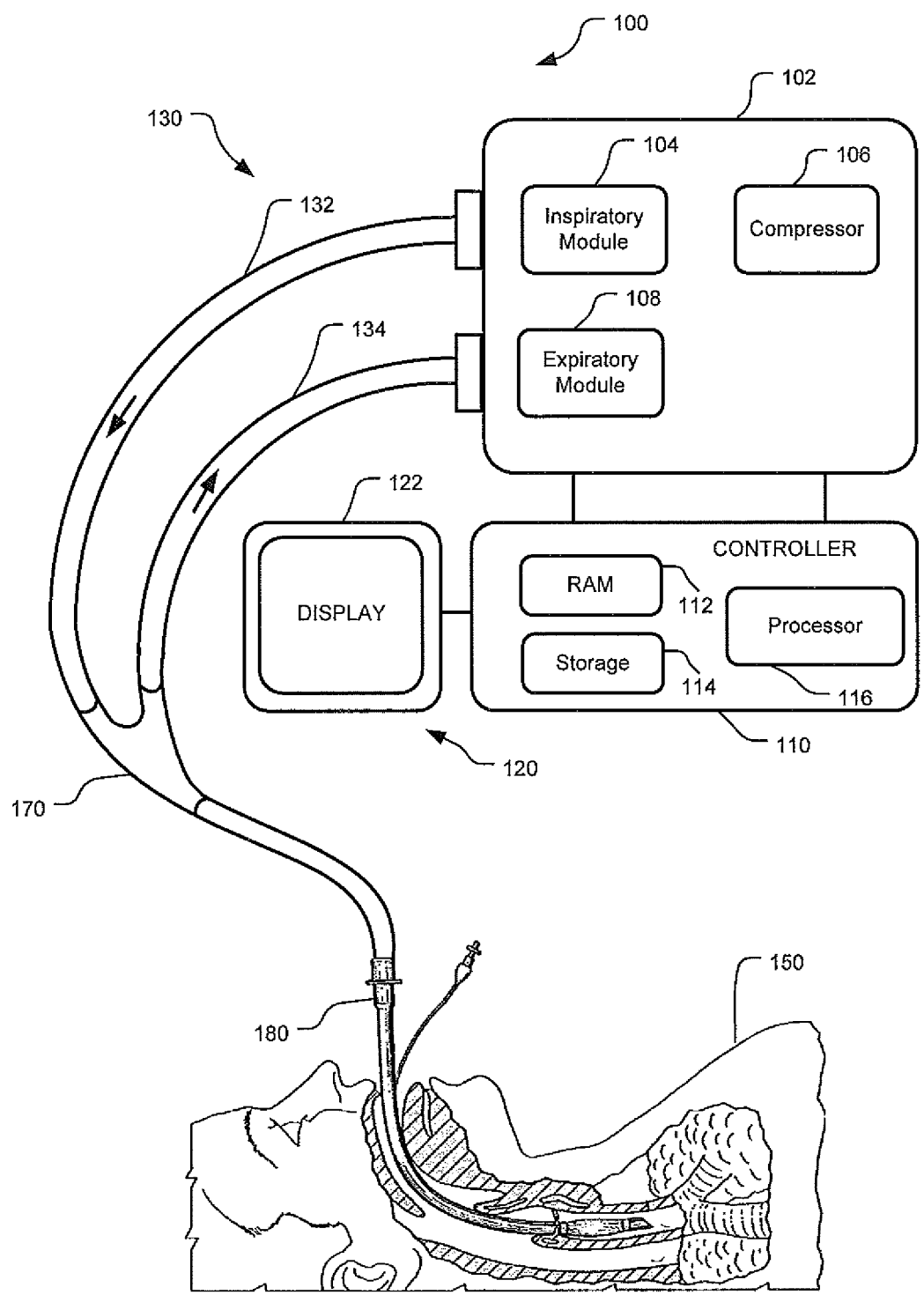
FIG. 1 is a diagram illustrating an embodiment of an exemplary ventilator connected to a human patient.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive (e.g., endotracheal tube, as shown) or a non-invasive (e.g., nasal mask) patient interface.

Ventilation tubing system 130 may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 to provide a gas source for ventilatory support via inspiratory limb 132.

The pneumatic system 102 may include a variety of other components, including mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type commonly found in command and control computing devices. In the depicted example, operator interface 120 includes a display 122 that may be touch-sensitive and/or voice-activated, enabling the display to serve both as an input and output device.

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Communication between components of the ventilatory system or between the ventilatoty system and other therapeutic equipment and/or remote monitoring systems may be conducted over a distributed network, as described further herein, via wired or wireless means. Further, the present methods may be configured as a presentation layer built over the TCP/IP protocol. TCP/IP stands for "Transmission Control Protocol/Internet Protocol" and provides a basic communication language for many local networks (such as intra- or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Ventilator Components

Figure 2:
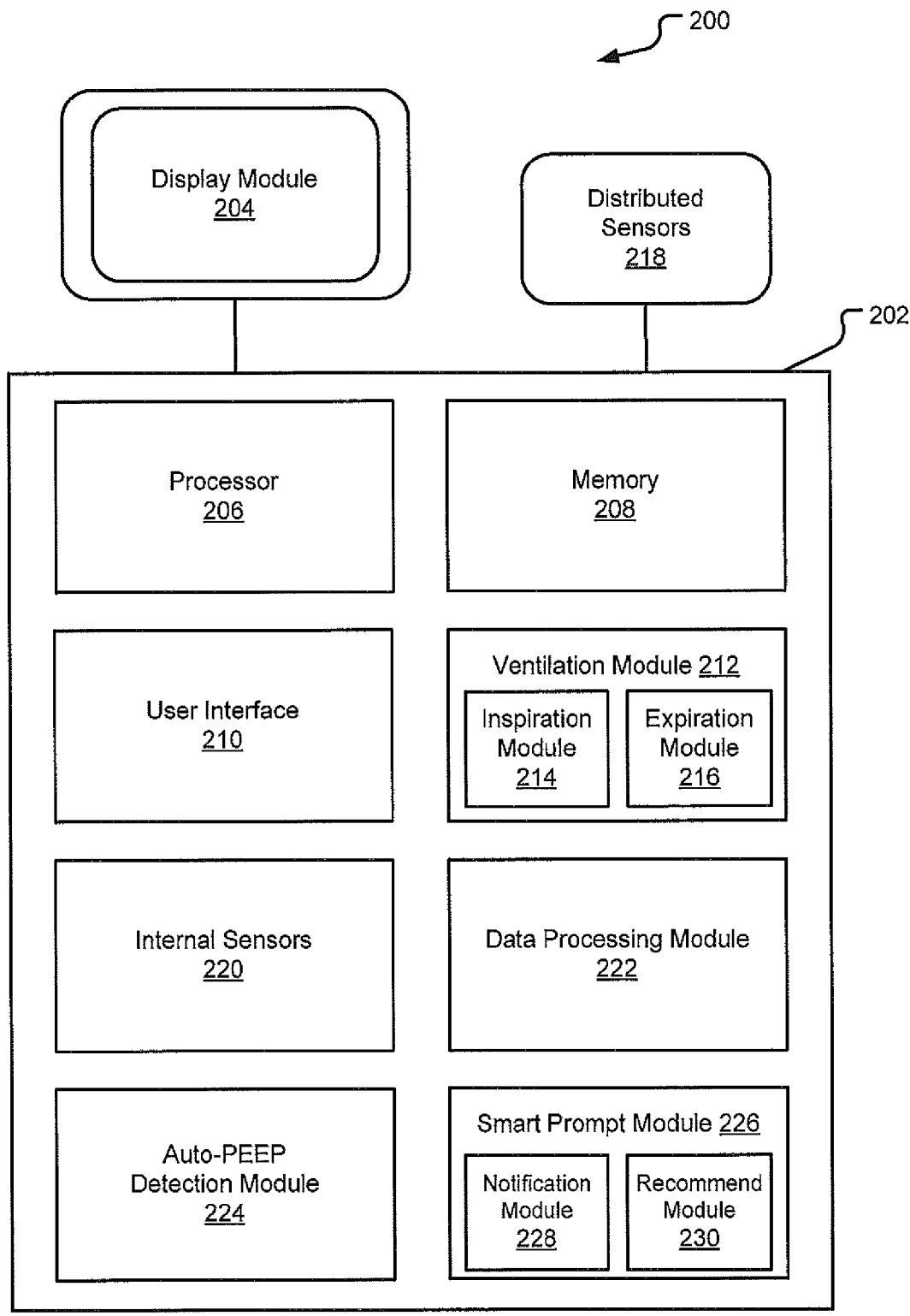
FIG. 2 is a block-diagram illustrating an embodiment of a ventilatory system for monitoring and evaluating ventilatory parameters associated with Auto-PEEP.

FIG. 2 is a block-diagram illustrating an embodiment of a ventilatory system for monitoring and evaluating ventilatory parameters associated with Auto-PEEP.

Ventilatory system 200 includes ventilator 202 with its various modules and components. That is, ventilator 202 may further include, inter alia, memory 208, one or more processors 206, user interface 210, and ventilation module 212 (which may further include an inspiration module 214 and an expiration module 216). Memory 208 is defined as described above for memory 112. Similarly, the one or more processors 206 are defined as described above for one or more processors 116. Processors 206 may further be configured with a clock whereby elapsed time may be monitored by the system 200.

The ventilatory system 200 may also include a display module 204 communicatively coupled to ventilator 202. Display module 204 provides various input screens, for receiving clinician input, and various display screens, for presenting useful information to the clinician. The display module 204 is configured to communicate with user interface 210 and may include a graphical user interface (GUI). The GUI may be an interactive display, e.g., a touch-sensitive screen or otherwise, and may provide various windows and elements for receiving input and interface command operations. Alternatively, the GUI may provide other suitable means of communication with the ventilator 202, for instance by a wheel, keyboard, mouse, or other suitable interactive device. Thus, user interface 210 may accept commands and input through display module 204. Display module 204 may also provide useful information in the form of various ventilatory data regarding the physical condition of a patient and/or a prescribed respiratory treatment. The useful information may be derived by the ventilator 202, based on data collected by a data processing module 222, and the useful information may be displayed to the clinician in the form of graphs, wave representations, pie graphs, or other suitable forms of graphic display. For example, one or more smart prompts may be displayed on the GUI and/or display module 204 upon detection of an implication of Auto-PEEP by the ventilator. Additionally or alternatively, one or more smart prompts may be communicated to a remote monitoring system coupled via any suitable means to the ventilatory system 200.

Equation of Motion

Ventilation module 212 may oversee ventilation of a patient according to prescribed ventilatory settings. By way of general overview, the basic elements impacting ventilation may be described by the following ventilatory equation (also known as the Equation of Motion):

$$P_m + P_v = V_T/C + R*F$$

Here, $P_m$ is a measure of muscular effort that is equivalent to the pressure generated by the muscles of a patient. If the patient's muscles are inactive, the $P_m$ is equivalent to 0 cm $H_2O$. During inspiration, $P_v$, represents the positive pressure delivered by a ventilator (generally in cm $H_2O$). $V_T$ represents the tidal volume delivered, C refers to the respiratory compliance, R represents the respiratory resistance, and F represents the gas flow during inspiration (generally in liters per min (L/m)). Alternatively, during expiration, the Equation of Motion may be represented as:

$$P_a + P_t = V_{TE}/C + R*F$$

Here, $P_a$ represents the positive pressure existing in the lungs (generally in cm $H_2O$), $P_t$ represents the transairway pressure, $V_{TE}$ represents the tidal volume exhaled, C refers to the respiratory compliance, R represents the respiratory resistance, and F represents the gas flow during expiration (generally in liters per min (L/m)).

Pressure

For positive pressure ventilation, pressure at the upper airway opening (e.g., in the patient's mouth) is positive relative to the pressure at the body's surface (i.e., relative to the ambient atmospheric pressure to which the patient's body surface is exposed, about 0 cm $H_2O$). As such, when $P_v$ is zero, i.e., no ventilatory pressure is being delivered, the upper airway opening pressure will be equal to the ambient pressure (i.e., about 0 cm $H_2O$). However, when ventilatory pressure is applied, a pressure gradient is created that allows gases to flow into the airway and ultimately into the lungs of a patient during inspiration (or, inhalation).

According to embodiments, additional pressure measurements may be obtained and evaluated. For example, transairway pressure, $P_t$, which refers to the pressure differential or gradient between the upper airway opening and the alveoli, may also be determined. $P_t$ may be represented mathematically as:

$$P_t = P_{awo} - P_a$$

Where $P_{awo}$ refers to the pressure in the upper airway opening, or mouth, and $P_a$ refers to the pressure within the alveolar space, or the lungs (as described above). $P_t$ may also be represented as follows:

$$P_t = F*R$$

Where F refers to flow and R refers to respiratory resistance, as described below, Additionally, lung pressure or alveolar pressure, $P_a$, may be measured or derived. For example, $P_a$ may be measured via a distal pressure transducer or other sensor near the lungs and/or the diaphragm. Alternatively, $P_a$ may be estimated by measuring the plateau pressure, $P_{Plat}$, via a proximal pressure transducer or other sensor at or near the airway opening. Plateau pressure, $P_{Plat}$, refers to a slight plateau in pressure that is observed at the end of inspiration when inspiration is held for a period of time, sometimes referred to as an inspiratory hold or pause maneuver, or a breath-hold maneuver. That is, when inspiration is held, pressure inside the alveoli and mouth are equal (i.e., no gas flow). However, as a result of muscular relaxation and elastance of the lungs during the hold period, forces are exerted on the inflated lungs that create a positive pressure. This positive pressure is observed as a plateau in the pressure waveform that is slightly below the peak inspiratory pressure, $P_{Peak}$, prior to initiation of expiration. As may be appreciated, for accurate measurement of $P_{Plat}$, the patient should be sedated or non-spontaneous (as muscular effort during the inspiratory pause may skew the pressure measurement). Upon determining $P_{Plat}$ based on the pressure waveform or otherwise, $P_{Plat}$ may be used as an estimate of $P_a$ (alveolar pressure).

Flow and Volume

Volume refers to the amount of gas delivered to a patient's lungs, usually in liters (L). Flow refers to a rate of change in volume over time ($F = \Delta V/\Delta t$). Flow is generally expressed in liters per minute (L/m or lpm) and, depending on whether gases are flowing into or out of the lungs, flow may be referred to as inspiratory flow or expiratory flow, respectively. According to embodiments, the ventilator may control the rate of delivery of gases to the patient, i.e., inspiratory flow, and may control the rate of release of gases from the patient, i.e., expiratory flow.

As may be appreciated, volume and flow are closely related. That is, where flow is known or regulated, volume may be derived based on elapsed times. Indeed, volume may be derived by integrating the flow waveform. According to embodiments, a tidal volume, $V_T$, may be delivered upon reaching a set inspiratory time ($T_I$) at set inspiratory flow. Alternatively, set $V_T$ and set inspiratory flow may determine the amount of time required for inspiration, i.e., $T_I$.

Respiratory Compliance

Additional ventilatory parameters that may be measured and/or derived may include respiratory compliance and respiratory resistance, which refer to the load against which the patient and/or the ventilator must work to deliver gases to the lungs. Respiratory compliance may be interchangeably referred to herein as compliance. Generally, compliance refers to a relative ease with which something distends and is the inverse of elastance, which refers to the tendency of something to return to its original form after being deformed. As related to ventilation, compliance refers to the lung volume achieved for a given amount of delivered pressure ($C = \Delta V/\Delta P$). Increased compliance may be detected when the ventilator measures an increased volume relative to the given amount of delivered pressure. Some lung diseases (e.g., acute respiratory distress syndrome (ARDS)) may decrease compliance and, thus, require increased pressure to inflate the lungs. Alternatively, other lung diseases may increase compliance, e.g., emphysema, and may require less pressure to inflate the lungs.

Additionally or alternatively, static compliance and dynamic compliance may be calculated. Static compliance, $C_S$, represents compliance impacted by elastic recoil at zero flow (e.g., of the chest wall, patient circuit, and alveoli). As elastic recoil of the chest wall and patient circuit may remain relatively constant, static compliance may generally represent compliance as affected by elastic recoil of the alveoli. As described above, $P_{Plat}$ refers to a slight plateau in pressure that is observed after relaxation of pleural muscles and elastic recoil, i.e., representing pressure delivered to overcome elastic forces. As such, $P_{Plat}$ provides a basis for estimating $C_s$ as follows:

$$C_S = V_T/(P_{Plat} - EEP)$$

Where $V_T$ refers to tidal volume, $P_{Plat}$ refers to plateau pressure, and EEP refers to end-expiratory pressure, or baseline pressure (including PEEP and/or Auto-PEEP), as discussed below. Note that proper calculation of $C_S$ depends on accurate measurement of $V_T$ and $P_{Plat}$.

Dynamic compliance, $C_D$, is measured during airflow and, as such, is impacted by both elastic recoil and airway resistance. Peak inspiratory pressure, $P_{Peak}$, which represents the highest pressure measured during inspiration, i.e., pressure delivered to overcome both elastic and resistive forces to inflate the lungs, is used to calculate $C_D$ as follows:

$$C_D = V_T/(P_{Peak} - EEP)$$

Where $V_T$ refers to tidal volume, $P_{Peak}$ refers to peak inspiratory pressure, and EEP refers to end-expiratory pressure. According to embodiments, ventilatory data may be more readily available for trending compliance of non-triggering patients than of triggering patients.

Respiratory Resistance

Respiratory resistance refers to frictional forces that resist airflow, e.g., due to synthetic structures (e.g., endotracheal tube, expiratory valve, etc.), anatomical structures (e.g., bronchial tree, esophagus, etc.), or viscous tissues of the lungs and adjacent organs. Respiratory resistance may be interchangeably referred to herein as resistance. Resistance is highly dependant on the diameter of the airway. That is, a larger airway diameter entails less resistance and a higher concomitant flow. Alternatively, a smaller airway diameter entails higher resistance and a lower concomitant flow. In fact, decreasing the diameter of the airway results in an exponential increase in resistance (e.g., two-times reduction of diameter increases resistance by sixteen times). As may be appreciated, resistance may also increase due to a restriction of the airway that is the result of, inter alia, increased secretions, bronchial edema, mucous plugs, brochospasm, and/or kinking of the patient interface (e.g., invasive endotracheal or tracheostomy tubes).

Airway resistance may further be represented mathematically as:

$$R = P_t/F$$

Where $P_t$ refers to the transairway pressure and F refers to the flow. That is, $P_t$ refers to the pressure necessary to overcome resistive forces of the airway. Resistance may be expressed in centimeters of water per liter per second (i.e., cm $H_2O$/L/s).

Pulmonary Time Constant

As discussed above, compliance refers to the lung volume achieved for a given amount of delivered pressure ($C = \Delta V/\Delta P$). That is, stated differently, volume delivered is equivalent to the compliance multiplied by the delivered pressure ($\Delta V = C \ast \Delta P$). However, as the lungs are not perfectly elastic, a period of time is needed to deliver the volume $\Delta V$ at pressure $\Delta P$. A pulmonary time constant, $\tau$, may represent a time necessary to inflate or exhale a given percentage of the volume at delivered pressure $\Delta P$. The pulmonary time constant, $\tau$, may be calculated by multiplying the respiratory resistance by the respiratory compliance ($\tau = R \ast C$) for a given patient and $\tau$ is generally represented in seconds, s. The pulmonary time constant associated with exhalation of the given percentage of volume may be termed an expiratory time constant and the pulmonary time constant associated with inhalation of the given percentage of volume may be termed an inspiratory time constant.

According to some embodiments, when expiratory resistance data is available, the pulmonary time constant may be calculated by multiplying expiratory resistance by compliance. According to alternative embodiments, the pulmonary time constant may be calculated based on inspiratory resistance and compliance. According to further embodiments, the expiratory time, $T_E$, should be equal to or greater than three (3) pulmonary time constants to ensure adequate exhalation. That is, for a triggering patient, $T_E$ (e.g., determined by trending $T_E$ or otherwise) should be equal to or greater than 3 pulmonary time constants. For a non-triggering patient, set RR should yield a $T_E$ that is equal to or greater than 3 pulmonary time constants.

Normal Resistance and Compliance

According to embodiments, normal respiratory resistance and compliance may be determined based on a patient's predicted body weight (PBW) (or ideal body weight (IBW)). That is, according to a standardized protocol or otherwise, patient data may be compiled such that normal respiratory resistance and compliance values and/or ranges of values may be determined and provided to the ventilatory system. That is, a manufacturer, clinical facility, clinician, or otherwise, may configure the ventilator with normal respiratory resistance and compliance values and/or ranges of values based on PBWs (or IBWs) of a patient population. Thereafter, during ventilation of a particular patient, respiratory resistance and compliance data may be trended for the patient and compared to normal values and/or ranges of values based on the particular patient's PBW (or IBW). According to embodiments, the ventilator may give an indication to the clinician regarding whether the trended respiratory resistance and compliance data of the particular patient falls into normal ranges. According to some embodiments, data may be more readily available for trending resistance and compliance for non-triggering patients than for triggering patients.

According to further embodiments, a predicted $T_E$ may be determined based on a patient's PBW (or IBW). That is, according to a standardized protocol or otherwise, patient population data may be compiled such that predicted $T_E$ values and/or ranges of values may be determined based on PBWs (or IBWs) of the patient population and provided to the ventilatory system. Actual (or trended) $T_E$ for a particular patient may then be compared to the predicted $T_E$. As noted previously, increased resistance and/or compliance may result in an actual $T_E$ that is longer than predicted $T_E$. However, when actual $T_E$ is consistent with predicted $T_E$, this may indicate that resistance and compliance for the particular patient fall into normal ranges.

According to further embodiments, a normal pulmonary time constant, $\tau$, may be determined based on a patient's PBW (or IBW). That is, according to a standardized protocol or otherwise, patient population data may be compiled such that normal $\tau$ values and/or ranges of values may be determined based on PBWs (or IBWs) of the patient population and provided to the ventilatory system. A calculated τ may be determined for a particular patient by multiplying resistance by compliance (as described above, resistance and compliance data may be more readily available for a non-triggering patient). As the product of resistance and compliance results in τ, increased resistance and/or compliance may result in an elevated τ value. However, when the calculated τ value for the particular patient is consistent with the normal τ value, this may indicate that the resistance and compliance of the particular patient fall into normal ranges.

Obstructive Component

Some patients may exhibit an obstructive component due to various conditions and diseases, e.g., COPD, ARDS, etc. That is, an obstructive component may be associated with patients that exhibit chronic elevated resistance due to constricted airways, alveolar collapse, etc. According to some embodiments, patients having these conditions may also exhibit elevated compliance. According to embodiments, determination of Auto-PEEP and/or determination of appropriate recommendations for mitigating Auto-PEEP may vary for patients exhibiting an obstructive component. As such, the ventilator may be configured to detect an obstructive component and/or may receive an indication from the clinician regarding whether the patient has been diagnosed with an obstructive disease. According to embodiments, when an obstructive component is detected, the ventilator may be configured with adjusted sensitivity to Auto-PEEP and/or may be configured to alter one or more recommendations for mitigating Auto-PEEP based on the detection of an obstructive component.

According to embodiments, normal respiratory resistance and compliance may be determined based on a patient's PBW (or IBW), as described above. During ventilation of a specific patient, respiratory resistance and compliance data may be trended for the patient and compared to normal values and/or ranges of values based on the specific patient's PBW (or IBW). According to embodiments, the ventilator may alert the clinician when the trended respiratory resistance and/or compliance data of the particular patient fall outside normal ranges. For example, when resistance data for a particular patient falls outside normal ranges, the ventilator may alert the clinician that the patient may have an obstructive component.

According to further embodiments, predicted $T_E$ may be determined based on a patient's PBW (or IBW), as described above. Actual (or trended) $T_E$ for a particular patient may then be compared to the predicted $T_E$. When actual $T_E$ is greater than predicted $T_E$, this may indicate that resistance and/or compliance of the particular patient falls outside normal ranges. When compliance has not changed, an elevated $T_E$ may be attributable to resistance and the ventilator may alert the clinician that the patient may have an obstructive component.

According to further embodiments, a normal pulmonary time constant, τ, may be determined based on a patient's PBW (or IBW), as described above. A calculated τ may be determined for a particular patient by multiplying resistance by compliance. When the calculated τ value is greater than the normal τ value, this may indicate that resistance and/or compliance for the particular patient fall outside normal ranges. When compliance has not changed, the elevated $T_E$ may be attributable to resistance and the ventilator may alert the clinician that the patient may have an obstructive component.

According to further embodiments, a clinician may input a patient diagnosis, e.g., COPD or emphysema. The ventilator may associate the patient diagnosis with certain lung and airway characteristics. For example, if the ventilator receives a patient diagnosis of COPD, the ventilator may associate this patient diagnosis with elevated resistance. Further, the ventilator may associate COPD with an obstructive component. Alternatively, if the ventilator receives a patient diagnosis of emphysema, the ventilator may associate this patient diagnosis with elevated compliance.

Inspiration

Ventilation module 212 may further include an inspiration module 214 configured to deliver gases to the patient according to prescribed ventilatory settings. Specifically, inspiration module 214 may correspond to the inspiratory module 104 or may be otherwise coupled to source(s) of pressurized gases (e.g., air, oxygen, and/or helium), and may deliver gases to the patient. Inspiration module 214 may be configured to provide ventilation according to various ventilatory modes, e.g., via volume-targeted, pressure-targeted, or via any other suitable mode of ventilation.

Volume ventilation refers to various forms of volume-targeted ventilation that regulate volume delivery to the patient. Different modes of volume ventilation are available depending on the specific implementation of volume regulation. For example, for volume-cycled ventilation, an end of inspiration is determined based on monitoring the volume delivered to the patient. Volume ventilation may include volume-control (VC), volume-assist, or volume assist/control ventilation. Volume ventilation may be accomplished by setting a target volume, or prescribed tidal volume, $V_T$, for delivery to the patient. According to embodiments, prescribed $V_T$ and inspiratory time ($T_I$) may be set during ventilation start-up, based on the patient's PBW (or IBW). In this case, flow will be dependent on the prescribed $V_T$ and set $T_I$. Alternatively, prescribed $V_T$ and flow may be set and $T_I$ may result. According to some embodiments, a predicted $T_E$ may be determined based on normal respiratory and compliance values or value ranges based on the patient's PBW (or IBW). Additionally, a respiratory rate (RR) setting, generally in breaths/min, may be determined and configured. For a non-triggering patient, the RR will control the timing for each inspiration. For a triggering patient, the RR setting will apply if the patient stops triggering for some reason and/or the patient's triggered RR drops below a threshold level.

According to embodiments, during volume ventilation, as volume and flow are regulated by the ventilator, delivered $V_T$, flow waveforms (or flow traces), and volume waveforms may be constant and may not be affected by variations in lung or airway characteristics (e.g., respiratory compliance and/or respiratory resistance). Alternatively, pressure readings may fluctuate based on lung or airway characteristics. According to some embodiments, the ventilator may control the inspiratory flow and then derive volume based on the inspiratory flow and elapsed time. For volume-cycled ventilation, when the derived volume is equal to the prescribed $V_T$, the ventilator may initiate expiration.

According to alternative embodiments, the inspiration module 214 may provide ventilation via a form of pressure ventilation. Pressure-targeted modes of ventilation may be provided by regulating the pressure delivered to the patient in various ways. For example, during pressure-cycled ventilation, an end of inspiration is determined based on monitoring the pressure delivered to the patient. Pressure ventilation may include pressure-support ventilation (PSV) or pressure-control ventilation (PCV), for example. Pressure ventilation may also include various forms of bi-level (BL) pressure ventilation, i.e., pressure ventilation in which the inspiratory positive airway pressure (IPAP) is higher than the expiratory positive airway pressure (EPAP). Specifically, pressure ventilation may be accomplished by setting a target or prescribed pressure for delivery to the patient. As for volume ventilation, predicted $T_I$ may be determined based on normal respiratory and compliance values and on the patient's PBW (or IBW). According to some embodiments, a predicted $T_E$ may be determined based on normal respiratory and compliance values and based on the patient's PBW (or IBW). A respiratory rate (RR) setting may also be determined and configured. For a non-triggering patient, the RR will control the timing for each inspiration. For a triggering patient, the RR setting will apply if the patient stops triggering for some reason and/or patient triggering drops below a threshold RR level.

According to embodiments, during pressure ventilation, the ventilator may maintain the same pressure waveform at the mouth, $P_{awo}$, regardless of variations in lung or airway characteristics, e.g., respiratory compliance and/or respiratory resistance. However, the volume and flow waveforms may fluctuate based on lung and airway characteristics. As noted above, pressure delivered to the upper airway creates a pressure gradient that enables gases to flow into a patient's lungs. The pressure from which a ventilator initiates inspiration is termed the end-expiratory pressure KEEP) or "baseline" pressure. This pressure may be atmospheric pressure (about 0 cm $H_2O$), also referred to as zero end-expiratory pressure (ZEEP). However, commonly, the baseline pressure may be positive, termed positive end-expiratory pressure (PEEP). Among other things, PEEP may promote higher oxygenation saturation and/or may prevent alveolar collapse during expiration. Under pressure-cycled ventilation, upon delivering the prescribed pressure the ventilator may initiate expiration.

According to still other embodiments, a combination of volume and pressure ventilation may be delivered to a patient, e.g., volume-targeted-pressure-controlled (VC+) ventilation. In particular, VC+ ventilation may provide benefits of setting a target $V_T$, while also allowing for monitoring variations in flow. As will be detailed further below, variations in flow may be indicative of various patient conditions.

Expiration

Ventilation module 212 may further include an expiration module 216 configured to release gases from the patient's lungs according to prescribed ventilatory settings. Specifically, expiration module 216 may correspond to expiratory module 108 or may otherwise be associated with and/or controlling an expiratory valve for releasing gases from the patient. By way of general overview, a ventilator may initiate expiration based on lapse of an inspiratory time setting ($T_I$) or other cycling criteria set by the clinician or derived from ventilator settings (e.g., detecting delivery of prescribed $V_T$ or prescribed pressure based on a reference trajectory). Upon initiating the expiratory phase, expiration module 216 may allow the patient to exhale by opening an expiratory valve. As such, expiration is passive, and the direction of airflow, as described above, is governed by the pressure gradient between the patient's lungs (higher pressure) and the ambient surface pressure (lower pressure). Although expiratory flow is passive, it may be regulated by the ventilator based on the size of the expiratory valve opening.

Expiratory time ($T_E$) is the time from the end of inspiration until the patient triggers for a spontaneously breathing patient. For a non-triggering patient, it is the time from the end of inspiration until the next inspiration based on the set RR. In some cases, however, the time required to return to the functional residual capacity (FRC) or resting capacity of the lungs is longer than provided by $T_E$ (e.g., because the patient triggers prior to fully exhaling or the RR is too high for a non-triggering patient). According to embodiments, various ventilatory settings may be adjusted to better match the time to reach FRC with the time available to reach FRC. For example, increasing flow will shorten $T_I$, thereby increasing the amount of time available to reach FRC. Alternatively, $V_T$ may be decreased, resulting in less time required to reach FRC.

As may be further appreciated, at the point of transition between inspiration and expiration, the direction of airflow may abruptly change from flowing into the lungs to flowing out of the lungs or vice versa depending on the transition. Stated another way, inspiratory flow may be measurable in the ventilatory circuit until $P_{Peak}$ is reached, at which point flow is zero. Thereafter, upon initiation of expiration, expiratory flow is measurable in the ventilatory circuit until the pressure gradient between the lungs and the body's surface reaches zero (again, resulting in zero flow). However, in some cases, as will be described further herein, expiratory flow may still be positive, i.e., measurable, at the end of expiration (termed positive end-expiratory flow or positive EEF). In this case, positive EEF is an indication that the pressure gradient has not reached zero or, similarly, that the patient has not completely exhaled. Although a single occurrence of premature inspiration may not warrant concern, repeated detection of positive EEF may be indicative of Auto-PEEP.

Ventilator Synchrony and Patient Triggering

According to some embodiments, the inspiration module 214 and/or the expiration module 216 may be configured to synchronize ventilation with a spontaneously-breathing, or triggering, patient. That is, the ventilator may be configured to detect patient effort and may initiate a transition from expiration to inspiration (or from inspiration to expiration) in response. Triggering refers to the transition from expiration to inspiration in order to distinguish it from the transition from inspiration to expiration (referred to as cycling). Ventilation systems, depending on their mode of operation, may trigger and/or cycle automatically, or in response to a detection of patient effort, or both.

Specifically, the ventilator may detect patient effort via a pressure-monitoring method, a flow-monitoring method, direct or indirect measurement of nerve impulses, or any other suitable method. Sensing devices may be either internal or distributed and may include any suitable sensing device, as described further herein. In addition, the sensitivity of the ventilator to changes in pressure and/or flow may be adjusted such that the ventilator may properly detect the patient effort, i.e., the lower the pressure or flow change setting the more sensitive the ventilator may be to patient triggering.

According to embodiments, a pressure-triggering method may involve the ventilator monitoring the circuit pressure, as described above, and detecting a slight drop in circuit pressure. The slight drop in circuit pressure may indicate that the patient's respiratory muscles, $P_m$, are creating a slight negative pressure gradient between the patient's lungs and the airway opening in an effort to inspire. The ventilator may interpret the slight drop in circuit pressure as patient effort and may consequently initiate inspiration by delivering respiratory gases.

Alternatively, the ventilator may detect a flow-triggered event. Specifically, the ventilator may monitor the circuit flow, as described above. If the ventilator detects a slight drop in flow during exhalation, this may indicate, again, that the patient is attempting to inspire. In this case, the ventilator is detecting a drop in bias flow (or baseline flow) attributable to a slight redirection of gases into the patient's lungs (in response to a slightly negative pressure gradient as discussed above). Bias flow refers to a constant flow existing in the circuit during exhalation that enables the ventilator to detect expiratory flow changes and patient triggering. For example, while gases are generally flowing out of the patient's lungs during expiration, a drop in flow may occur as some gas is redirected and flows into the lungs in response to the slightly negative pressure gradient between the patient's lungs and the body's surface. Thus, when the ventilator detects a slight drop in flow below the bias flow by a predetermined threshold amount (e.g., 2 L/min below bias flow), it may interpret the drop as a patient trigger and may consequently initiate inspiration by delivering respiratory gases.

Ventilator Sensory Devices

The ventilatory system 200 may also include one or more distributed sensors 218 communicatively coupled to ventilator 202. Distributed sensors 218 may communicate with various components of ventilator 202, e.g., ventilation module 212, internal sensors 220, data processing module 222, Auto-PEEP detection module 224, and any other suitable components and/or modules. Distributed sensors 218 may detect changes in ventilatory parameters indicative of Auto-PEEP, for example. Distributed sensors 218 may be placed in any suitable location, e.g., within the ventilatory circuitry or other devices communicatively coupled to the ventilator. For example, sensors may be affixed to the ventilatory tubing or may be imbedded in the tubing itself. According to some embodiments, sensors may be provided at or near the lungs (or diaphragm) for detecting a pressure in the lungs. Additionally or alternatively, sensors may be affixed or imbedded in or near wye-fitting 170 and/or patient interface 180, as described above.

Distributed sensors 218 may further include pressure transducers that may detect changes in circuit pressure (e.g., electromechanical transducers including piezoelectric, variable capacitance, or strain gauge). Distributed sensors 218 may further include various flowmeters for detecting airflow (e.g., differential pressure pneumotachometers). For example, some flowmeters may use obstructions to create a pressure decrease corresponding to the flow across the device (e.g., differential pressure pneumotachometers) and other flowmeters may use turbines such that flow may be determined based on the rate of turbine rotation (e.g., turbine flowmeters). Alternatively, sensors may utilize optical or ultrasound techniques for measuring changes in ventilatory parameters. A patient's blood parameters or concentrations of expired gases may also be monitored by sensors to detect physiological changes that may be used as indicators to study physiological effects of ventilation, wherein the results of such studies may be used for diagnostic or therapeutic purposes. Indeed, any distributed sensory device useful for monitoring changes in measurable parameters during ventilatory treatment may be employed in accordance with embodiments described herein.

Ventilator 202 may further include one or more internal sensors 220. Similar to distributed sensors 218, internal sensors 220 may communicate with various components of ventilator 202, e.g., ventilation module 212, internal sensors 220, data processing module 222, Auto-PEEP detection module 224, and any other suitable components and/or modules. Internal sensors 220 may employ any suitable sensory or derivative technique for monitoring one or more parameters associated with the ventilation of a patient. However, the one or more internal sensors 220 may be placed in any suitable internal location, such as, within the ventilatory circuitry or within components or modules of ventilator 202. For example, sensors may be coupled to the inspiratory and/or expiratory modules for detecting changes in, for example, circuit pressure and/or flow. Specifically, internal sensors may include pressure transducers and flowmeters for measuring changes in circuit pressure and airflow. Additionally or alternatively, internal sensors may utilize optical or ultrasound techniques for measuring changes in ventilatory parameters. For example, a patient's expired gases may be monitored by internal sensors to detect physiological changes indicative of the patient's condition and/or treatment, for example. Indeed, internal sensors may employ any suitable mechanism for monitoring parameters of interest in accordance with embodiments described herein.

As should be appreciated, with reference to the Equation of Motion, ventilatory parameters are highly interrelated and, according to embodiments, may be either directly or indirectly monitored. That is, parameters may be directly monitored by one or more sensors, as described above, or may be indirectly monitored by derivation according to the Equation of Motion.

Ventilatory Data

Ventilator 202 may further include a data processing module 222. As noted above, distributed sensors 218 and internal sensors 220 may collect data regarding various ventilatory parameters. A ventilatory parameter refers to any factor, characteristic, or measurement associated with the ventilation of a patient, whether monitored by the ventilator or by any other device. Sensors may further transmit collected data to the data processing module 222 and, according to embodiments, the data processing module may 222 be configured to collect data regarding some ventilatory parameters, to derive data regarding other ventilatory parameters, and to graphically represent collected and derived data to the clinician and/or other modules of the ventilatory system. Some collected, derived, and/or graphically represented data may be indicative of Auto-PEEP. For example, data regarding end-expiratory flow (EEF), data regarding alveolar pressure $P_a$ (e.g., via a breath-hold maneuver as described above), $P_{Peak}$ data, $P_{plat}$ data, volume data, flow trace data, EEP data etc., may be collected, derived, and/or graphically represented by data processing module 222.

Flow Data

For example, according to embodiments, data processing module 222 may be configured to monitor inspiratory and expiratory flow. Flow may be measured by any appropriate, internal or distributed device or sensor within the ventilatory system. As described above, flowmeters may be employed by the ventilatory system to detect circuit flow. However, any suitable device either known or developed in the future may be used for detecting airflow in the ventilatory circuit.

Data processing module 222 may be further configured to plot monitored flow data graphically via any suitable means. For example, according to embodiments, flow data may be plotted versus time (flow waveform), versus volume (flow-volume loop), or versus any other suitable parameter as may be useful to a clinician. According to embodiments, flow may be plotted such that each breath may be independently identified. Further, flow may be plotted such that inspiratory flow and expiratory flow may be independently identified, e.g., inspiratory flow may be represented in one color and expiratory flow may be represented in another color. According to additional embodiments, flow waveforms and flow-volume loops, for example, may be represented alongside additional graphical representations, e.g., representations of volume, pressure, etc., such that clinicians may substantially simultaneously visualize a variety of ventilatory parameters associated with each breath.

As may be appreciated, flow decreases as resistance increases, making it more difficult to pass gases into and out of the lungs (i.e., $F=P_t/R$). For example, when a patient is intubated, i.e., having either an endotracheal or a tracheostomy tube in place, resistance may be increased as a result of the smaller diameter of the tube over a patient's natural airway. In addition, increased resistance may be observed in patients with obstructive disorders, such as COPD, asthma, etc. Higher resistance may necessitate, inter alia, a higher inspiratory time setting ($T_I$) for delivering a prescribed pressure or volume of gases, a higher flow setting for delivering prescribed pressure or volume, a lower respiratory rate resulting in a higher expiratory time ($T_E$) for complete exhalation of gases, etc.

Specifically, changes in flow may be detected by evaluating various flow data. For example, by evaluating FV loops, as described above, an increase in resistance may be detected over a number of breaths. That is, upon comparing consecutive FV loops, the expiratory plot for each FV loop may reflect a progressive reduction in expiratory flow (i.e., a smaller FV loop), indicative of increasing resistance. According to other embodiments, an evaluation of end-expiratory flow (EEF) may be used to detect Auto-PEEP, as described further herein. For example, if EEF has not reduced to zero before inspiration begins, this may indicate that gases may still be trapped in the lungs (e.g., insufficient $T_E$ to return to FRC or elevated FRC).

Pressure Data

According to embodiments, data processing module 222 may be configured to monitor pressure. Pressure may be measured by any appropriate, internal or distributed device or sensor within the ventilatory system. For example, pressure may be monitored by proximal electromechanical transducers connected near the airway opening (e.g., on the inspiratory limb, expiratory limb, at the patient interface, etc.). Alternatively, pressure may be monitored distally, at or near the lungs and/or diaphragm of the patient.

For example, $P_{Peak}$ and/or $P_{Plat}$ (estimating $P_a$) may be measured proximally (e.g., at or near the airway opening) via single-point pressure measurements. According to embodiments, $P_{Plat}$ (estimating $P_a$) may be measured during an inspiratory pause maneuver (e.g., expiratory and inspiratory valves are closed briefly at the end of inspiration for measuring the $P_{Plat}$ at zero flow). According to other embodiments, circuit pressure may be measured during an expiratory pause maneuver (e.g., expiratory and inspiratory valves are closed briefly at the end of expiration for measuring EEP at zero flow). In this case, set PEEP may be subtracted from measured EEP for detecting Auto-PEEP. Alternatively, $P_a$ may be distally measured (e.g., at or near the lungs and/or diaphragm) via multiple-point pressure measurements. This method may also be useful for detecting Auto-PEEP at the end of expiration. According to some embodiments, triggering patients may need to be sedated before taking some of the above-described pressure measurements.

Data processing module 222 may be further configured to plot monitored pressure data graphically via any suitable means. For example, according to embodiments, pressure data may be plotted versus time (pressure waveform), versus volume (pressure-volume loop or PV loop), or versus any other suitable parameter as may be useful to a clinician. According to embodiments, pressure may be plotted such that each breath may be independently identified. Further, pressure may be plotted such that inspiratory pressure and expiratory pressure may be independently identified, e.g., inspiratory pressure may be represented in one color and expiratory pressure may be represented in another color. According to additional embodiments, pressure waveforms and PV loops, for example, may be represented alongside additional graphical representations, e.g., representations of volume, flow, etc., such that a clinician may substantially simultaneously visualize a variety of parameters associated with each breath.

According to embodiments, PV loops may provide useful clinical and diagnostic information to clinicians regarding the respiratory resistance or compliance of a patient. Specifically, upon comparing PV loops from successive breaths, an increase in resistance may be detected when successive PV loops shorten and widen over time. That is, at constant pressure, less volume is delivered to the lungs when resistance is increasing, resulting in a shorter, wider PV loop. According to alternative embodiments, a PV loop may provide a visual representation, in the area between the inspiratory plot of pressure vs. volume and the expiratory plot of pressure vs. volume, which is indicative of respiratory compliance. Further, PV loops may be compared to one another to determine whether compliance has changed. Additionally or alternatively, optimal compliance may be determined. That is, optimal compliance may correspond to the dynamic compliance determined from a PV loop during a recruitment maneuver, for example.

According to additional embodiments, PV curves may be used to compare $C_S$ and $C_D$ over a number of breaths. For example, a first PV curve may be plotted for $C_S$ (based on $P_{Plat}$ less EEP) and a second PV curve may be plotted for $C_D$ (based on $P_{Peak}$ less EEP). Under normal conditions, $C_S$ and $C_D$ curves may be very similar, with the $C_D$ curve mimicking the $C_S$ curve but shifted to the right (i.e., plotted at higher pressure). However, in some cases the $C_D$ curve may flatten out and shift to the right relative to the $C_S$ curve. This graphical representation may illustrate increasing $P_r$, and thus increasing R, which may be due to mucous plugging or bronchospasm, for example. In other cases, both the $C_D$ curve and the $C_S$ curves may flatten out and shift to the right. This graphical representation may illustrate an increase in $P_{Peak}$ and $P_{Plat}$, without an increase in $P_r$, and thus may implicate a decrease in lung compliance, which may be due to tension pneumothorax, atelectasis, pulmonary edema, pneumonia, bronchial intubation, etc.

As may be further appreciated, relationships between resistance, static compliance, dynamic compliance, and various pressure readings may give indications of patient condition. For example, when $C_S$ increases, $C_D$ increases and, similarly, when R increases, $C_D$ increases. Additionally, as discussed previously, $P_r$ represents the difference in pressure attributable to resistive forces over elastic forces. Thus, where $P_{Peak}$ and $P_r$ are increasing with constant $V_T$ delivery, R is increasing (i.e., where $P_{Peak}$ is increasing without a concomitant increase in $P_{Plat}$). Where $P_r$ is roughly constant, but where $P_{Peak}$ and $P_{Plat}$ are increasing with a constant $V_T$ delivery, $C_S$ is increasing.

Volume Data

According to embodiments, data processing module 222 may be configured to derive volume via any suitable means. For example, as described above, during volume ventilation, a prescribed $V_T$ may be set for delivery to the patient. The actual volume delivered may be derived by monitoring the inspiratory flow over time (i.e., V=F*T). Stated differently, integration of flow over time will yield volume. According to embodiments, $V_T$ is completely delivered upon reaching $T_I$. Similarly, the expiratory flow may be monitored such that expired tidal volume ($V_{TE}$) may be derived. That is, under ordinary conditions, upon reaching the $T_E$, the prescribed $V_T$ delivered should be completely exhaled and FRC should be reached. However, under some conditions $T_E$ is inadequate for complete exhalation and FRC is not reached.

Data processing module 222 may be further configured to plot derived volume data graphically via any suitable means. For example, according to embodiments, volume data may be plotted versus time (volume waveform), versus flow (flow-volume loop or FV loop), or versus any other suitable parameter as may be useful to a clinician. According to embodiments, volume may be plotted such that each breath may be independently identified. Further, volume may be plotted such that prescribed $V_T$ and $V_{TE}$ may be independently identified, e.g., prescribed $V_T$ may be represented in one color and $V_{TE}$ may be represented in another color. According to additional embodiments, volume waveforms and FV loops, for example, may be represented alongside additional graphical representations, e.g., representations of pressure, flow, etc., such that a clinician may substantially simultaneously visualize a variety of parameters associated with each breath.

Auto-PEEP Detection

Ventilator 202 may further include an Auto-PEEP detection module 224. As described above, the pressure from which a ventilator initiates inspiration is termed the end-expiratory pressure (EEP) and, when EEP is positive, it is termed positive end-expiratory pressure (PEEP). PEEP may be prescribed by a clinician for various reasons. For example, for some patients (e.g., ARDS patients), PEEP may be prescribed for supporting oxygenation and preventing alveolar collapse at the end of expiration. PEEP may also allow a reduction of $F_1O_2$ (fraction inspired oxygen) to safe levels, However, in some cases, additional gases, i.e., in addition to the prescribed PEEP, may be trapped in the lungs at the end of expiration. This condition may be commonly referred to as Auto-PEEP, or intrinsic PEEP. That is, at the end of expiration, when PEEP is prescribed, EEP is equal to PEEP plus Auto-PEEP; and, where PEEP is not prescribed, EEP is equal to Auto-PEEP.

More specifically, in some cases, Auto-PEEP may result when the lungs are not sufficiently emptied during expiration before inspiration is initiated. For example, during volume ventilation of a non-triggering patient, the ventilator may regulate transitions between inspiration and expiration and between expiration and inspiration as well as the respiratory rate (RR), $V_T$, flow, etc. In this case, gas-trapping may result when RR is too high, $V_T$ is too high, flow is too low, $T_I$ is too long and/or $T_E$ is too short, etc. Alternatively, during volume ventilation of a triggering patient, the patient triggers the transition between expiration and inspiration, i.e., the RR. In this case, gas-trapping may result when inspiration is triggered before expiration is complete, e.g., when $V_T$ is too high, flow is too low, $T_I$ is too long (resulting in $T_E$ being insufficient before patient-triggering occurs). Specifically, when incomplete exhalation occurs, gases may be trapped in the lungs, resulting in an increased FRC. Indeed, with each breath, additional gases may be trapped and, not surprisingly, Auto-PEEP has been linked to barotrauma and an increase in the work of breathing (WOB), among other conditions.

Barotrauma may result from the over-distension of alveoli, which may cause disruption of the alveolar epithelium. Further, as pressure in the alveoli increases, some alveoli may rupture, allowing gases to seep into the perivascular sheath and into the mediastinum. This condition may be referred to as pulmonary interstitial emphysema (PIE). Further complications associated with PIE may result in a pneumothorax (i.e., partial to complete collapse of a lung due to gases collected in the pleural cavity). Additionally or alternatively, Auto-PEEP has been associated with impeded venous return, which may lead to reduced cardiac output. Patients suffering from acute respiratory distress syndrome (ARDS) or acute lung injury (ALI) may be especially susceptible to Auto-PEEP. The work of breathing (WOB) refers to the amount of energy required to inhale, i.e., against forces that oppose inspiration as described above. For spontaneously-breathing patients, an increased WOB may lead to exhaustion of the respiratory muscles. Indeed, an increased WOB may further damage and/or compromise a patient's ability to provide at least some muscular effort during respiration—potentially extending their time on ventilation.

According to embodiments, Auto-PEEP may occur as a result of various patient conditions and/or inappropriate ventilatory settings. Thus, according to embodiments, Auto-PEEP detection module 224 may evaluate various ventilatory parameter data based on one or more predetermined thresholds to detect the presence of Auto PEEP. For example, the Auto-PEEP detection module 224 may evaluate expiratory flow on a flow waveform, or flow trace, to determine whether EEF has reached zero before inspiration begins. That is, if EEF breaches a predetermined threshold (e.g., EEF exceeds about 5 L/m), the pressure gradient between the patient's lungs and the ambient surface pressure has likely not reached zero. As such, it is likely that gases have not been completely exhaled. This condition may occur when inspiration is initiated automatically by the ventilator (e.g., for a non-triggering patient) or when inspiration is initiated via patient triggering (e.g., for a spontaneously-breathing patient). If this situation occurs over several breaths, it may implicate trapping of gases, or Auto-PEEP. Thus, when EEF is positive (i.e., breaches the predetermined threshold) for several consecutive or substantially consecutive breaths (e.g., positive EEF detected three or more times in ten consecutive breaths), the Auto-PEEP detection module 224 may detect an implication of Auto-PEEP. As may be appreciated, the threshold values disclosed herein are provided as examples only. Indeed, threshold values may be determined via any suitable standard protocol or otherwise. Alternatively, threshold values may be determined and configured for a specific patient according to a specific prescription or otherwise.

According to further embodiments, Auto-PEEP detection module 224 may evaluate expiratory flow on a flow trace to detect patient effort for a triggering patient. That is, by evaluating the slope of the expiratory flow curve, the Auto-PEEP detection module 224 may determine that the patient attempted to trigger while the patient was still actively exhaling. That is, if $T_I$ is set too high, the ventilator may take too long to deliver the prescribed $V_T$. Thereafter, a triggering patient may attempt to initiate another inspiration prior to complete exhalation of gases, potentially trapping gases in the lungs. Thus, when patient triggering is detected during active exhalation, the Auto-PEEP detection module 224 may detect an implication of Auto-PEEP.

According to further embodiments, Auto-PEEP detection module 224 may utilize the flow waveform to evaluate inspiratory flow based on one or more predetermined thresholds. For example, if pressure exists in the lungs (e.g., due to Auto-PEEP), gases may not begin to flow into the lungs until the pressure in the mouth exceeds the lung pressure (i.e., until a pressure gradient is established). That is, inspiratory flow may be slowed at the beginning of inspiration if Auto-PEEP is present. As such, the Auto-PEEP detection module 224 may be configured to detect whether inspiratory flow fails to exceed a predetermined threshold within a certain amount of time after initiation of inspiration (e.g., as automatically initiated by the ventilator based on parameter settings for a non-triggering patient or initiated based on ventilator detection of patient effort and/or neural indications for a triggering patient). Thus, when inspiratory flow breaches a predetermined threshold at the beginning of inspiration, the Auto-PEEP detection module 224 may detect an implication of Auto-PEEP.

According to further embodiments, Auto-PEEP detection module 224 may evaluate various ventilatory parameters to determine whether respiratory resistance is increasing. As described previously, increased resistance may cause a decrease in flow. Consequently, $T_E$ may not be adequate for complete exhalation to FRC. Resistance may increase for a number of reasons, as listed above, including ascites (fluid build-up in the peritoneal cavity surrounding the lungs that may increase viscous tissue resistance), chronic obstructive pulmonary disease (COPD), asthma, emphysema, mucous blockage, or otherwise. In some cases, a clinician may be aware of a patient's obstructive condition; however, it may be desirable for the ventilator to detect whether an obstructive disorder is worsening. Alternatively, it may be desirable for the ventilator to detect whether an obstructive disorder developing or whether resistance is increasing for some other reason.

For example, Auto-PEEP detection module 224 may monitor ventilatory data based on one or more predetermined thresholds to determine whether resistance is increasing. For example, where $P_t$ is increasing with constant $V_T$ delivery, resistance may be increasing. Further, where flow is decreasing with constant $P_t$, resistance may be increasing (i.e., $R=P_t/F$). For example, if resistance increases by a predetermined threshold, Auto-PEEP may be implicated (e.g., resistance increases by about 5 cm $H_2O/L/s$ or more). As may be appreciated, the threshold values disclosed herein are provided as examples only. Indeed, threshold values may be determined via any suitable standard protocol or otherwise. Alternatively, threshold values may be determined and configured for a specific patient according to a specific prescription or otherwise.

Alternatively, the Auto-PEEP detection module 224 may evaluate PV curves to compare $C_S$ and $C_D$ over a number of breaths to detect whether respiratory resistance is increasing, as described above. That is, when the $C_D$ curve flattens out and shifts to the right relative to the $C_S$ curve, this may indicate that $P_t$ is increasing and, thus, that resistance is increasing. Generally, based on the above evaluations, an inspiratory resistance may be trended over a period of time. However, according to other embodiments, expiratory resistance may also be evaluated. For example, by comparing consecutive FV loops, an expiratory plot for each FV loop may reflect a progressive reduction in expiratory flow indicative of increasing resistance. Consequently, if $T_E$ is not long enough for complete exhalation at the decreased flow, gases may be trapped in the lungs.

Alternatively, the Auto-PEEP detection module 224 may evaluate PV loops from successive breaths to detect an increase in resistance. For example, increased resistance may be detected when successive PV loops shorten and widen over time. That is, at constant pressure, less volume is delivered to the lungs when resistance is increasing, resulting in a shorter, wider PV loop.

Alternatively, the Auto-PEEP detection module 224 may evaluate the expiratory limb resistance of the patient circuit to detect increased resistance. Where resistance of the expiratory limb breaches a predetermined threshold, the ventilator may recommend that the clinician check the exhalation filter for mucous or other obstruction that may be causing elevated expiratory limb resistance. According to further embodiments, as increased expiratory limb resistance may prevent complete exhalation, Auto-PEEP may be implicated.

As may be appreciated from the above examples, an increase in resistance may be detected by evaluating graphical data in the form of PV curves, PV loops and/or FV loops. That is, the ventilator may determine that resistance has increased by evaluating changes in the graphical data and/or changes in the underlying data corresponding to the graphical data. Alternatively, an increase in resistance may be detected by calculation, e.g., by measuring flow and pressure and by calculating resistance (i.e., where compliance is constant). However, according to embodiments, when increased resistance is detected via any suitable method, the Auto-PEEP detection module 224 may detect an implication of Auto-PEEP.

According to further embodiments, Auto-PEEP detection module 224 may evaluate various ventilatory parameters to determine whether respiratory compliance is increasing. That is, when elastance decreases (e.g., forces opposing lung inflation), it may require less pressure to deliver a particular volume (i.e., $\Delta V=C^*\Delta P$). Consequently, additional volume may be delivered at constant pressure and may over-distend the lungs and/or result in gas-trapping. For example, Auto-PEEP detection module 224 may evaluate PV loops based on one or more predetermined thresholds to detect whether compliance is increasing, i.e., by comparing the area between the inspiratory plot of pressure vs. volume and the expiratory plot of pressure vs. volume over a number of breaths. According to alternative embodiments, Auto-PEEP detection module 224 may evaluate PV curves to compare $C_S$ and $C_D$ over a number of breaths, as described above. That is, where both the $C_D$ curve and the $C_S$ curve straighten and shift to the left (e.g., illustrating decreasing $P_{Peak}$ and $P_{Plat}$) compliance may be increasing. Alternatively, the ventilator may be configured with a predetermined threshold increase for compliance (e.g., an increase of about 10 mL/cmH$_2$O or more), such that Auto-PEEP may be implicated when compliance breaches the predetermined threshold increase. That is, if compliance increases, less pressure may be required to deliver a prescribed $V_T$ and/or lower $T_I$ may be required to deliver the prescribed $V_T$. Thus, if adjustments are not made, Auto-PEEP may result.

As may be appreciated from the above examples, an increase in compliance may be detected by evaluating graphical data associated with PV loops or PV curves. That is, the ventilator may determine that respiratory compliance has increased by evaluating changes in the graphical data and/or changes in the underlying data corresponding to the graphical data. Alternatively, an increase in compliance may be calculated, e.g., by determining $V_T$, $P_{Plat}$ and EEP to calculate $C_S$ or by determining $V_T$, $P_{Peak}$, and EEP to calculate $C_D$. In either case, when increased compliance is detected, the Auto-PEEP detection module 224 may detect an implication of Auto-PEEP.

According to further embodiments, the Auto-PEEP detection module 224 may calculate the pulmonary time constant by multiplying resistance (e.g., expiratory resistance) by compliance for a particular patient. Additionally, the Auto-PEEP detection module 224 may trend $T_E$ over multiple breaths. When $T_E$ is less than three pulmonary time constants, $T_E$ may not be adequate for complete exhalation and the Auto-PEEP detection module 224 may detect an implication of Auto-PEEP.

According to alternative embodiments, the Auto-PEEP detection module 224 may trend $T_E$ over multiple breaths based on one or more predetermined thresholds to detect whether $T_E$ is limited for a triggering patient. For example, if the respiratory rate (RR) is too high or flow is set too low, the $T_E$ may be limited. That is, for a triggering patient, $T_E$ may not be long enough to reach FRC before inspiration is triggered, potentially resulting in Auto-PEEP. For a non-triggering patient, the RR setting may be set too high such that $T_E$ is not long enough to reach FRC before the ventilator initiates inspiration. According to embodiments, a time required to reach FRC may be calculated, e.g., based on $V_T$ and resistance and compliance data. The time required to reach FRC may then be compared to $T_E$ to determine whether the time required to reach FRC is greater than $T_E$. When the time required to reach FRC is greater than $T_E$ by a predetermined threshold, for instance, it may be determined that $T_E$ is limited. Further, when limited $T_E$ is detected, the Auto-PEEP detection module 224 may detect an implication of Auto-PEEP.

According to further embodiments, the Auto-PEEP detection module 224 may evaluate data from an expiratory-pause maneuver. For example, an expiratory-pause maneuver may be conducted manually by a clinician or automatically at certain intervals during ventilation. During the expiratory-pause maneuver, expiratory and inspiratory valves may be momentarily shut at the end of expiration. For example, when the end-expiratory pressure (EEP) reading in the circuit exceeds set PEEP by a threshold amount (e.g., about 5 cm $H_2O$ above set PEEP), the presence of Auto-PEEP may be implicated. According to alternative embodiments, EEP readings may be taken by sensors at or near the patient's lungs and/or diaphragm to determine the presence of Auto-PEEP. Note that it is preferable that the patient be sedated or non-triggering for these measurements to be accurate. Thus, when EEP is greater than set PEEP at the end of expiration for a threshold number of breaths (e.g., three or more times in ten consecutive breaths), the Auto-PEEP detection module 224 may determine that Auto-PEEP is implicated. As may be appreciated, the threshold values disclosed herein are provided as examples only. Indeed, threshold values may be determined via any suitable standard protocol or otherwise. Alternatively, threshold values may be determined and configured for a specific patient according to a specific prescription or otherwise.

Smart-Prompt Generation

Ventilator 202 may further include a smart prompt module 226. As described above, the presence of Auto-PEEP may be very difficult for a clinician to detect. As may be appreciated, multiple ventilatory parameters may be monitored and evaluated in order to detect an implication of Auto-PEEP. In addition, when Auto-PEEP is implicated, many clinicians may not be aware of adjustments to ventilatory parameters that may reduce or eliminate Auto-PEEP. As such, upon detection of Auto-PEEP, the smart prompt module 226 may be configured to notify the clinician that Auto-PEEP is implicated and/or to provide recommendations to the clinician for mitigating Auto-PEEP. For example, smart prompt module 226 may be configured to notify the clinician by displaying a smart prompt on display monitor 204 and/or within a window of the GUI. According to additional embodiments, the smart prompt may be communicated to and/or displayed on a remote monitoring system communicatively coupled to ventilatory system 200. Alternatively, in an automated embodiment, the smart prompt module 226 may communicate with a ventilator control system so that the recommendation may be automatically implemented to mitigate Auto-PEEP.

In order to accomplish the various aspects of the notification and/or recommendation message display, the smart prompt module 226 may communicate with various other components and/or modules. For instance, smart prompt module 226 may be in communication with data processing module 222, Auto-PEEP detection module 224, or any other suitable module or component of the ventilatory system 200. That is, smart prompt module 226 may receive an indication that Auto-PEEP has been implicated by any suitable means. In addition, smart prompt module 226 may receive information regarding one or more parameters that implicated the presence of Auto-PEEP and information regarding the patient's ventilatory settings and treatment. Further, according to some embodiments, the smart prompt module 226 may have access to a patient's diagnostic information (e.g., regarding whether the patient has ARDS, COPD, asthma, emphysema, or any other disease, disorder, or condition).

Smart prompt module 226 may further comprise additional modules for making notifications and/or recommendations to a clinician regarding the presence of Auto-PEEP. For example, according to embodiments, smart prompt module 226 may include a notification module 228 and a recommendation module 230. For instance, smart prompts may be provided according to a hierarchical structure such that a notification messages and/or a recommendation message may be initially presented in summarized form and, upon clinician selection, an additional detailed notification and/or recommendation message may be displayed. According to alternative embodiments, a notification message may be initially presented and, upon clinician selection, a recommendation message may be displayed. Alternatively or additionally, the notification message may be simultaneously displayed with the recommendation message in any suitable format or configuration.

Specifically, according to embodiments, the notification message may alert the clinician as to the detection of a patient condition, a change in patient condition, or an effectiveness of ventilatory treatment. For example, the notification message may alert the clinician that Auto-PEEP has been detected. The notification message may further alert the clinician regarding the particular ventilatory parameter(s) that implicated Auto-PEEP (e.g., positive EEF over the last n breaths, decreased flow over the past n breaths at constant $V_T$, increased resistance, etc.)

Additionally, according to embodiments, the recommendation message may provide various suggestions to the clinician for addressing a detected condition. That is, if Auto-PEEP has been detected, the recommendation message may suggest that the clinician reduce $V_T$, increase flow, increase $T_E$ by decreasing RR and/or $T_I$, etc. According to additional embodiments, the recommendation message may be based on the particular ventilatory parameter(s) that implicated Auto-PEEP. Additionally or alternatively, the recommendation message may be based on current ventilatory settings such that suggestions are directed to a particular patient's treatment. Additionally or alternatively, the recommendation message may be based on a diagnosis and/or other patient attributes. Further still, the recommendation message may include a primary recommendation message and a secondary recommendation message.

As described above, smart prompt module 226 may also be configured with notification module 228 and recommendation module 230. The notification module 228 may be in communication with data processing module 222, Auto-PEEP detection module 224, or any other suitable module to receive an indication that Auto-PEEP has been detected. Notification module 228 may be responsible for generating a notification message via any suitable means. For example, the notification message may be provided as a tab, banner, dialog box, or other similar type of display. Further, the notification messages may be provided along a border of the graphical user interface, near an alarm display or bar, or in any other suitable location. A shape and size of the notification message may further be optimized for easy viewing with minimal interference to other ventilatory displays. The notification message may be further configured with a combination of icons and text such that the clinician may readily identify the message as a notification message.

The recommendation module 230 may be responsible for generating one or more recommendation messages via any suitable means. The one or more recommendation messages may provide suggestions and information regarding addressing a detected condition and may be accessible from the notification message. For example, the one or more recommendation messages may identify the parameters that implicated the detected condition, may provide suggestions for adjusting one or more ventilatory parameters to address the detected condition, may provide suggestions for checking ventilatory equipment or patient position, or may provide other helpful information. Specifically, the one or more recommendation messages may provide suggestions and information regarding Auto-PEEP.

According to embodiments, based on the particular parameters that implicated Auto-PEEP, the recommendation module may provide suggestions for addressing Auto-PEEP. That is, if Auto-PEEP was implicated by positive EEF over several breaths, the one or more recommendation messages may include suggesting increasing set flow, adjusting settings such that EEF approximates zero, lowering RR such that $T_E$ may be increased, lowering $V_T$ such that $T_E$ may be adequate, etc. Alternatively, if Auto-PEEP was implicated by increased resistance, the one or more recommendation messages may include suggesting suctioning the patient interface, adjusting patient position, delivering a bronchodialator or other suitable medication, etc.

Additionally or alternatively, the one or more recommendation messages may also be based on current ventilatory settings for the patient. For example, if Auto-PEEP was implicated by positive EEF over several breaths, but where the patient's current ventilatory settings include a high flow setting, the one or more recommendation messages may not suggest increasing set flow.

Additionally or alternatively, the one or more recommendation messages may be based on a patient's diagnosis or other clinical data. According to some embodiments, if a patient has been diagnosed with COPD, the ventilator may be configured with adjusted thresholds such that sensitivity to resistance is increased (i.e., a lower predetermined threshold) or decreased (i.e., a higher predetermined threshold) based on clinician input or otherwise. According to some embodiments, if a patient has been diagnosed with emphysema, the ventilator may be configured with adjusted thresholds such that sensitivity to compliance is increased (i.e., a lower predetermined threshold) or decreased (i.e., a higher predetermined threshold) based on clinician input or otherwise. According to other embodiments, if a patient has been diagnosed with ARDS, the ventilator may be aware that the patient is at higher risk for Auto-PEEP and may configured with increased sensitivity for detecting implications of Auto-PEEP. Alternatively, Auto-PEEP may be desirable for an ARDS patient (e.g., preventing alveolar collapse and increasing oxygenation) and the ventilator may be configured with decreased sensitivity for detecting implications of Auto-PEEP. When Auto-PEEP is detected, the one or more recommendation messages may include suggesting decreasing RR, increasing flow, increasing $T_E$, decreasing $V_T$, etc.

According to still other embodiments, the recommendation message may include a primary message and a secondary message. That is, a primary message may provide suggestions that are specifically targeted to the detected condition based on the particular parameters that implicated the condition. Alternatively, the primary message may provide suggestions that may provide a higher likelihood of mitigating the detected condition. The secondary message may provide more general suggestions and/or information that may aid the clinician in further addressing and/or mitigating the detected condition. For example, the primary message may provide a specific suggestion for adjusting a particular parameter to mitigate the detected condition (e.g., consider increasing flow and/or adjust settings such that EEF approximates zero). Alternatively, the secondary message may provide general suggestions for addressing the detected condition (e.g., consider other steps for increasing $T_E$ such as decreasing $V_T$ or switching to a square flow waveform).

Smart prompt module 226 may also be configured such that notification and/or recommendation messages may be displayed in a partially transparent window or format. The transparency may allow for notification and/or recommendation messages to be displayed such that normal ventilator GUI and respiratory data may be visualized behind the messages. This feature may be particularly useful for displaying detailed messages. As described previously, notification and/or recommendation messages may be displayed in areas of the display screen that are either blank or that cause minimal distraction from the respiratory data and other graphical representations provided by the GUI. However, upon selective expansion of a message, respiratory data and graphs may be at least partially obscured. As a result, translucent display may provide the detailed message such that it is partially transparent. Thus, graphical and other data may be visible behind the detailed alarm message.

Additionally, notification and/or recommendation messages may provide immediate access to the display and/or settings screens associated with the detected condition. For example, an associated parameter settings screen may be accessed from a notification and/or a recommendation message via a hyperlink such that the clinician may address the detected condition as necessary. An associated parameter display screen may also be accessed such that the clinician may view clinical data associated with the detected condition in the form of charts, graphs, or otherwise. That is, according to embodiments, the clinician may access the ventilatory data that implicated the detected condition for verification purposes. For example, when Auto-PEEP has been implicated, depending on the particular ventilatory parameters that implicated Auto-PEEP, the clinician may be able to access ventilatory settings for addressing Auto-PEEP (e.g., a settings screen for adjusting $V_T$, $T_I$, flow, etc.) and/or to view associated ventilatory parameters that implicated Auto-PEEP (e.g., a graphics screen displaying historical flow waveforms, volume waveforms, and/or pressure waveforms that gave rise to implications of Auto-PEEP).

According to embodiments, upon viewing the notification and/or recommendation messages, upon addressing the detected condition by adjusting one or more ventilatory settings or otherwise, or upon manual selection, the notification and/or recommendation messages may be cleared from the graphical user interface.

Auto-PEEP Detection During Volume Ventilation of Non-Triggering Patient

Figure 3:
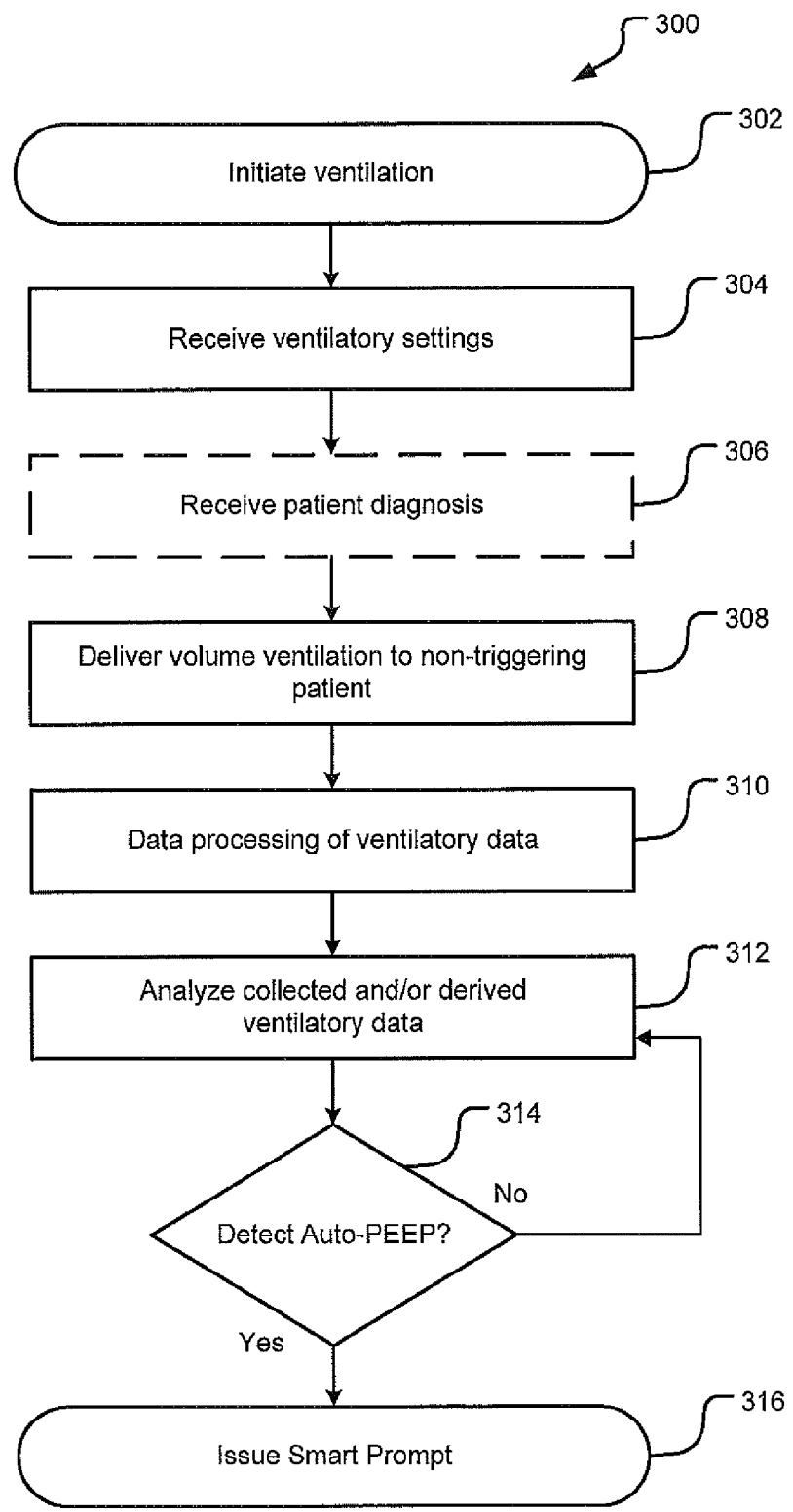
FIG. 3 is a flow chart illustrating an embodiment of a method for detecting an implication of Auto-PEEP.

FIG. 3 is a flow chart illustrating an embodiment of a method for detecting an implication of Auto-PEEP.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

The illustrated embodiment of the method 300 depicts a method for detecting Auto-PEEP during volume ventilation of a non-triggering patient. Method 300 begins with an initiate ventilation operation 302. Initiate ventilation operation 302 may further include various additional operations. For example, initiate ventilation operation 302 may include receiving one or more ventilatory settings associated with ventilation of a patient (e.g., at receive settings operation 304). For example, the ventilator may be configured to provide volume ventilation to a non-triggering patient. As such, the ventilatory settings and input received may include a prescribed $V_T$, set flow (or peak flow), predicted or ideal body weight (PBW or IBW), RR, etc. According to some embodiments, a predicted $T_E$ may be determined based on normal respiratory and compliance values or value ranges based on the patient's PBW or IBW. According to some embodiments, respiratory resistance and dynamic compliance data may be trended for the patient during ventilation to determine whether the data actually falls within normal ranges.

According to some embodiments, initiate ventilation operation 302 may further include receiving diagnostic information regarding the patient (e.g., at receive diagnosis operation 306, represented with dashed lines to identify the operation as optional). For example, according to embodiments, the clinician may indicate that the patient has been diagnosed with ARDS, COPD, emphysema, asthma, etc. The ventilator may be further configured to associate a patient diagnosis with various conditions (e.g., increased resistance associated with COPD, increased likelihood of alveolar collapse associated with ARDS, etc.).

At deliver ventilation operation 308, the ventilator provides volume ventilation to a non-triggering patient, as described above. That is, according to embodiments, the ventilator provides ventilation based on a prescribed $V_T$. For example, the ventilator may deliver gases to the patient at a set flow for a set $T_I$ at a set RR. When prescribed $V_T$ has been delivered, the ventilator may initiate the expiratory phase.

While volume ventilation is being delivered, the ventilator may conduct various data processing operations. For example, at data processing operation 310, the ventilator may collect and/or derive various ventilatory parameter data associated with volume ventilation of the non-triggering patient. For example, as described above, the ventilator may collect data regarding flow and pressure parameters. Additionally, the ventilator may derive various ventilatory parameter data based on the collected data, e.g., volume, respiratory resistance, respiratory compliance, etc. As described previously, measurements for respiratory resistance and/or compliance may be trended continuously for a non-triggering patient because ventilatory data may be obtained without sedating the patient or otherwise. Additionally, the ventilator may generate various graphical representations of the collected and/or derived ventilatory parameter data, e.g., flow waveforms, pressure waveforms, pressure-volume loops, flow-volume loops, etc.

At analyze operation 312, the ventilator may evaluate collected and/or derived data to determine whether a certain patient condition exists. For example, according to embodiments, the ventilator may evaluate the various collected and derived parameter data, including EEF, $T_E$, EEP, respiratory resistance and/or compliance, $P_a$, patient effort, etc., based on one or more predetermined thresholds. According to embodiments, the ventilator may further evaluate the ventilatory parameter data in light of the patient's specific parameter settings, including $V_T$, set flow, set $T_I$, etc., and/or the patient's diagnostic information.

According to some embodiments, at detect operation 314 the ventilator may determine whether Auto-PEEP is implicated based on evaluating EEF at analyze operation 312. For example, according to embodiments, the ventilator may be configured with a threshold value for EEF. For example, if EEF is greater than or equal to about 5 L/m when inspiration is initiated, the threshold may be breached and positive EEF may be detected (e.g., when EEF is greater than or equal to 5 L/m). Further, according to embodiments, the ventilator may be configured with a threshold number of breaths, e.g., if positive EEF is detected three or more times in ten consecutive breaths the threshold may be breached. That is, when three or more of ten consecutive breaths exhibit positive EEF, it may be determined that Auto-PEEP is implicated.

According to alternative embodiments, the ventilator may further take into account a patient's diagnosis to determine whether Auto-PEEP is likely, as described above. For example, if a patient has been diagnosed with ARDS, the ventilator may determine that Auto-PEEP is more likely and may be configured with additional sensitivity to changes in the above parameters (e.g., detection of positive EEF two or more times in ten consecutive breaths may breach a threshold for an ARDS patient). If Auto-PEEP is implicated, the operation may proceed to issue smart prompt operation 316. If Auto-PEEP is not implicated, the operation may return to analyze operation 312.

According to still other embodiments, at detect operation 314 the ventilator may determine whether Auto-PEEP is implicated based on evaluating EEP at analyze operation 312. According to embodiments, EEP may be measured distally via any suitable method (e.g., by one or more pressure transducers at or near the lungs and/or diaphragm). Alternatively, EEP may be measured proximally via any suitable method (e.g., during an expiratory hold maneuver). If EEP in excess of set PEEP (if any) is detected at the end of expiration, Auto-PEEP may be implicated. According to embodiments, the ventilator may be configured with a threshold value for EEP (e.g., about 5 cm $H_2O$ above set PEEP). Further, according to embodiments, the ventilator may be configured with a threshold number of breaths, e.g., excess pressure detected three or more times in ten consecutive breaths may breach the threshold. That is, when three or more of ten consecutive breaths exhibit excess pressure at the end of expiration, it may be determined that Auto-PEEP is implicated. If Auto-PEEP is implicated, the operation may proceed to issue smart prompt operation 316. If Auto-PEEP is not implicated, the operation may return to analyze operation 312.

According to other embodiments, at detect operation 314 the ventilator may determine whether Auto-PEEP is implicated based on evaluating resistance and/or compliance at analyze operation 312. According to embodiments, the ventilator may be configured with a predetermined threshold increase for resistance. For example, if resistance increases by about 5 cm $H_2O/L/s$ or more, it may be determined that Auto-PEEP is implicated. Alternatively, the ventilator may be configured with a predetermined threshold increase for compliance. For example, if compliance increases by about 10 mL/cm $H_2O$ or more, it may be determined that Auto-PEEP is implicated. If Auto-PEEP is implicated, the operation may proceed to issue smart prompt operation 316. If Auto-PEEP is not implicated, the operation may return to analyze operation 312.

According to other embodiments, at detect operation 314 the ventilator may evaluate respiratory resistance data and respiratory compliance data to calculate a time required to reach functional residual capacity (FRC). Thereafter, the time required to reach FRC may be compared to the $T_E$. According to embodiments, when the time required to reach FRC is greater than the $T_E$ by a predetermined threshold, it may be determined that Auto-PEEP is implicated. If Auto-PEEP is implicated, the operation may proceed to issue smart prompt operation 316. If Auto-PEEP is not implicated, the operation may return to analyze operation 312.

According to further embodiments, at detect operation 314 the ventilator may evaluate the pulmonary time constant and $T_E$. That is, by multiplying resistance (e.g., expiratory resistance) by compliance the ventilator may calculate the pulmonary time constant. The ventilator may also trend $T_E$ over multiple breaths for the non-triggering patient. When $T_E$ is less than three pulmonary time constants, $T_E$ may not be adequate for complete exhalation and the ventilator may detect an implication of Auto-PEEP. If Auto-PEEP is implicated, the operation may proceed to issue smart prompt operation 316. If Auto-PEEP is not implicated, the operation may return to analyze operation 312.

As may be appreciated, the ventilator may determine whether Auto-PEEP is implicated at detect operation 314 via any suitable means. Indeed, any of the above described ventilatory parameters may be evaluated according to various thresholds for detecting Auto-PEEP. Further, the disclosure regarding specific ventilatory parameters as they may implicate Auto-PEEP is not intended to be limiting. In fact, any suitable ventilatory parameter may be monitored and evaluated for detecting Auto-PEEP within the spirit of the present disclosure. As such, if Auto-PEEP is implicated via any suitable means, the operation may proceed to issue smart prompt operation 316. If Auto-PEEP is not implicated, the operation may return to analyze operation 312.

At issue smart prompt operation 316, the ventilator may alert the clinician via any suitable means that Auto-PEEP has been implicated. For example, according to embodiments, the ventilator may display a smart prompt including a notification message and/or a recommendation message regarding the detection of Auto-PEEP on the GUI. According to alternative embodiments, the ventilator may communicate the smart prompt, including the notification message and/or the recommendation message, to a remote monitoring system communicatively coupled to the ventilator.

According to embodiments, the notification message may alert the clinician that Auto-PEEP has been detected and, optionally, may provide information regarding the ventilatory parameter(s) that implicated Auto-PEEP. According to additional embodiments, the recommendation message may provide one or more suggestions for mitigating Auto-PEEP. According to further embodiments, the one or more suggestions may be based on the patient's particular ventilatory settings and/or diagnosis. According to some embodiments, the clinician may access one or more parameter setting and/or display screens from the smart prompt via a hyperlink or otherwise for addressing Auto-PEEP. According to additional or alternative embodiments, a clinician may remotely access one or more parameter and/or display screens from the smart prompt via a hyperlink or otherwise for remotely addressing Auto-PEEP.

Smart Prompt Generation Regarding Auto-PEEP Detection

Figure 4:
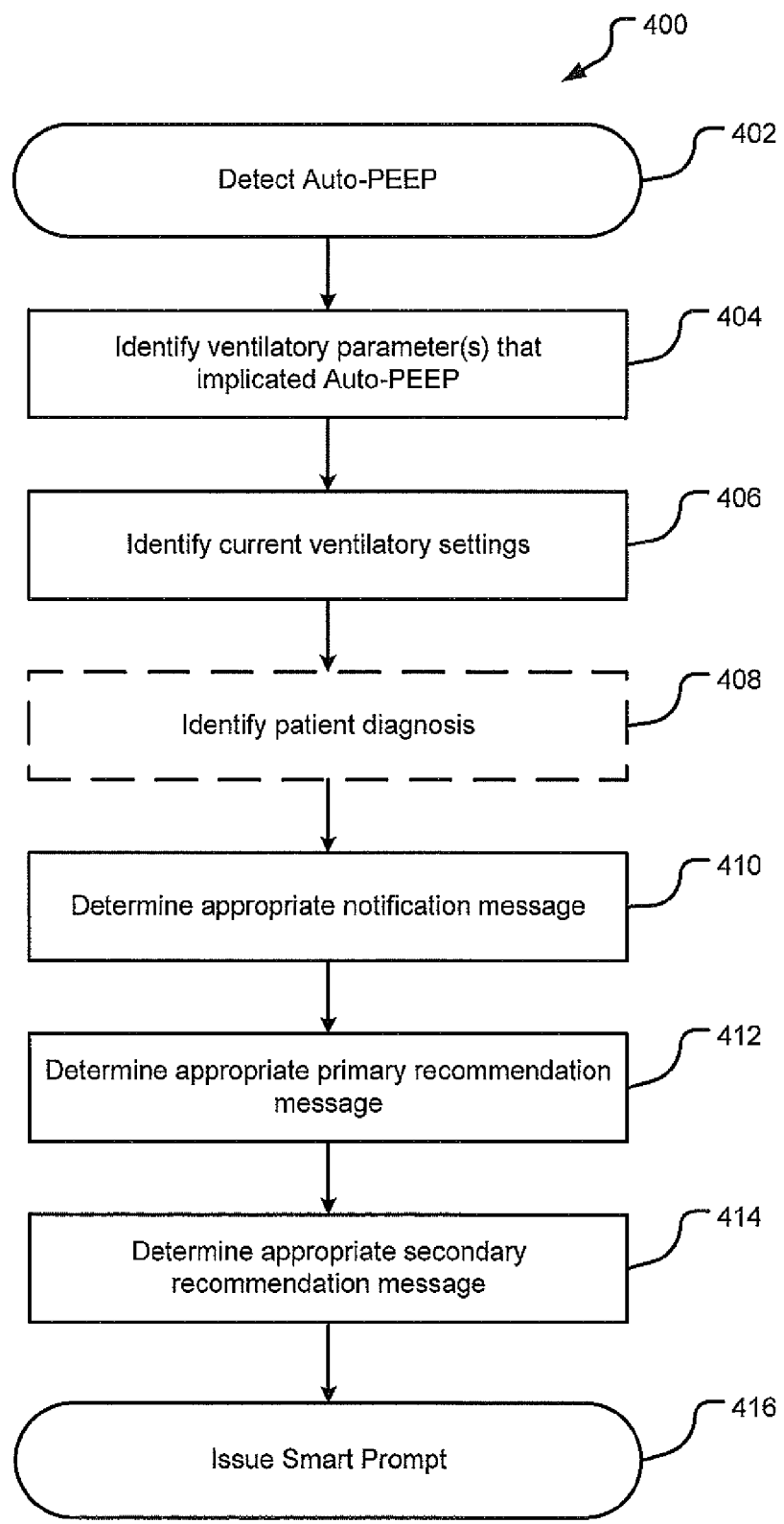
FIG. 4 is a flow chart illustrating an embodiment of a method for issuing a smart prompt upon detecting an implication of Auto-PEEP.

FIG. 4 is a flow chart illustrating an embodiment of a method for issuing a smart prompt upon detecting an implication of Auto-PEEP.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

The illustrated embodiment of the method 400 depicts a method for issuing a smart prompt upon detecting Auto-PEEP during volume ventilation of a non-triggering patient. Method 400 begins with detect operation 402, wherein the ventilator detects that Auto-PEEP is implicated, as described above in method 300.

At identify ventilatory parameters operation 404, the ventilator may identify one or more ventilatory parameters that implicated Auto-PEEP. For example, the ventilator may recognize that Auto-PEEP was implicated by positive EEF over several breaths. Alternatively, the ventilator may recognize that Auto-PEEP was implicated by excess EEP over PEEP. Alternatively, the ventilator may recognize that Auto-PEEP was implicated by increased resistance and/or compliance. Alternatively, the ventilator may recognize that Auto-PEEP was implicated by determining the time required to reach FRC is greater than $T_E$. As may be appreciated, the ventilator may use information regarding ventilatory parameters that implicated Auto-PEEP in determining an appropriate notification and/or recommendation message of the smart prompt.

At identify settings operation 406, the ventilator may identify one or more current ventilatory settings associated with the ventilatory treatment of the patient. For example, current ventilatory settings may have been received upon initiating ventilation for the patient and may have been determined by the clinician or otherwise (e.g., by evaluating a patient diagnosis, oxygenation, PBW or IBW, disease conditions, etc.). For instance, current ventilatory settings associated with volume ventilation for a non-triggering patient may include, inter alia, prescribed $V_T$, flow, RR, $T_I$, etc. In addition, a predicted TE may have been determined based on normal respiratory resistance and compliance values and the patient's PBW or IBW. As may be appreciated, the ventilator may use information regarding current ventilatory settings in determining an appropriate notification and/or recommendation message of the smart prompt.

At identify patient diagnosis operation 408, the ventilator may optionally identify patient diagnosis information received from a clinician (represented with dashed lines to identify the operation as optional). For example, according to embodiments, the clinician may indicate during ventilation initiation or otherwise that the patient was diagnosed with COPD, ARDS, emphysema, asthma, etc. As may be appreciated, the ventilator may use information regarding a patient's diagnosis in determining an appropriate notification and/or recommendation message of the smart prompt.

At determine operation 410, the ventilator may determine an appropriate notification message. For example, the appropriate notification message may alert the clinician that Auto-PEEP has been implicated and, optionally, may provide information regarding the ventilatory parameter(s) that implicated Auto-PEEP. For example, the appropriate notification may alert the clinician that Auto-PEEP was implicated by positive EEF over several breaths, Auto-PEEP was implicated by excess EEP over several breaths, or Auto-PEEP was implicated by increased resistance.

At determine operation 412, the ventilator may determine an appropriate primary recommendation message. The appropriate primary recommendation message may provide one or more specific suggestions for mitigating Auto-PEEP. For example, according to some embodiments, in determining the appropriate primary recommendation message, the ventilator may take into consideration the one or more monitored ventilatory parameters that implicated Auto-PEEP. That is, if Auto-PEEP was implicated by positive EEF over several breaths, the ventilator may offer one or more recommendation messages that may include: "Consider increasing respiratory rate and/or set flow to shorten $T_I$; Adjust settings until EEF approximates zero; Investigate reasons for increased resistance and/or compliance," for example. Alternatively, if Auto-PEEP was implicated by increased resistance, the one or more recommendation messages may include suggesting suctioning the patient interface, adjusting patient position, delivering a bronchodialator or other suitable medication, etc.

According to other embodiments, in determining an appropriate primary recommendation message the ventilator may take into consideration the patient's current ventilatory settings. That is, if set flow is already high, the ventilator may not suggest increasing the set flow. In this case, the primary recommendation message may rather suggest decreasing $V_T$, or may provide another suitable specific suggestion. According to further embodiments, in determining the appropriate primary recommendation message the ventilator may take into consideration the patient's diagnosis. For example, if a patient has been diagnosed with ARDS, in determining an appropriate primary recommendation message, the ventilator may make a specific suggestion for changing patient position rather than decreasing $V_T$ (e.g., as high $V_T$ may be necessary for adequate oxygenation of an ARDS patient).

At determine operation 414, the ventilator may determine an appropriate secondary recommendation message. The secondary recommendation message may provide one or more general suggestions for mitigating Auto-PEEP. For example, the secondary recommendation message may include: "Consider other steps for increasing $T_E$, such as decreasing $V_T$ or switching to a square flow waveform." The secondary recommendation message may provide additional recommendations for mitigating Auto-PEEP.

At issue smart prompt operation 416, the ventilator may alert the clinician via any suitable means that Auto-PEEP has been implicated. For example, according to embodiments, a smart prompt may include an appropriate notification message and an appropriate recommendation message regarding the presence of Auto-PEEP. Additionally or alternatively, the smart prompt may include an appropriate notification message, an appropriate primary recommendation message, and an appropriate secondary recommendation message. The smart prompt may be displayed via any suitable means, e.g., on the ventilator GUI and/or at a remote monitoring station, such that the clinician is alerted as to the potential presence of Auto-PEEP and offered additional information and/or recommendations for mitigating the Auto-PEEP, as described herein.

Ventilator GUI Display of Initial Smart Prompt

Figure 5:
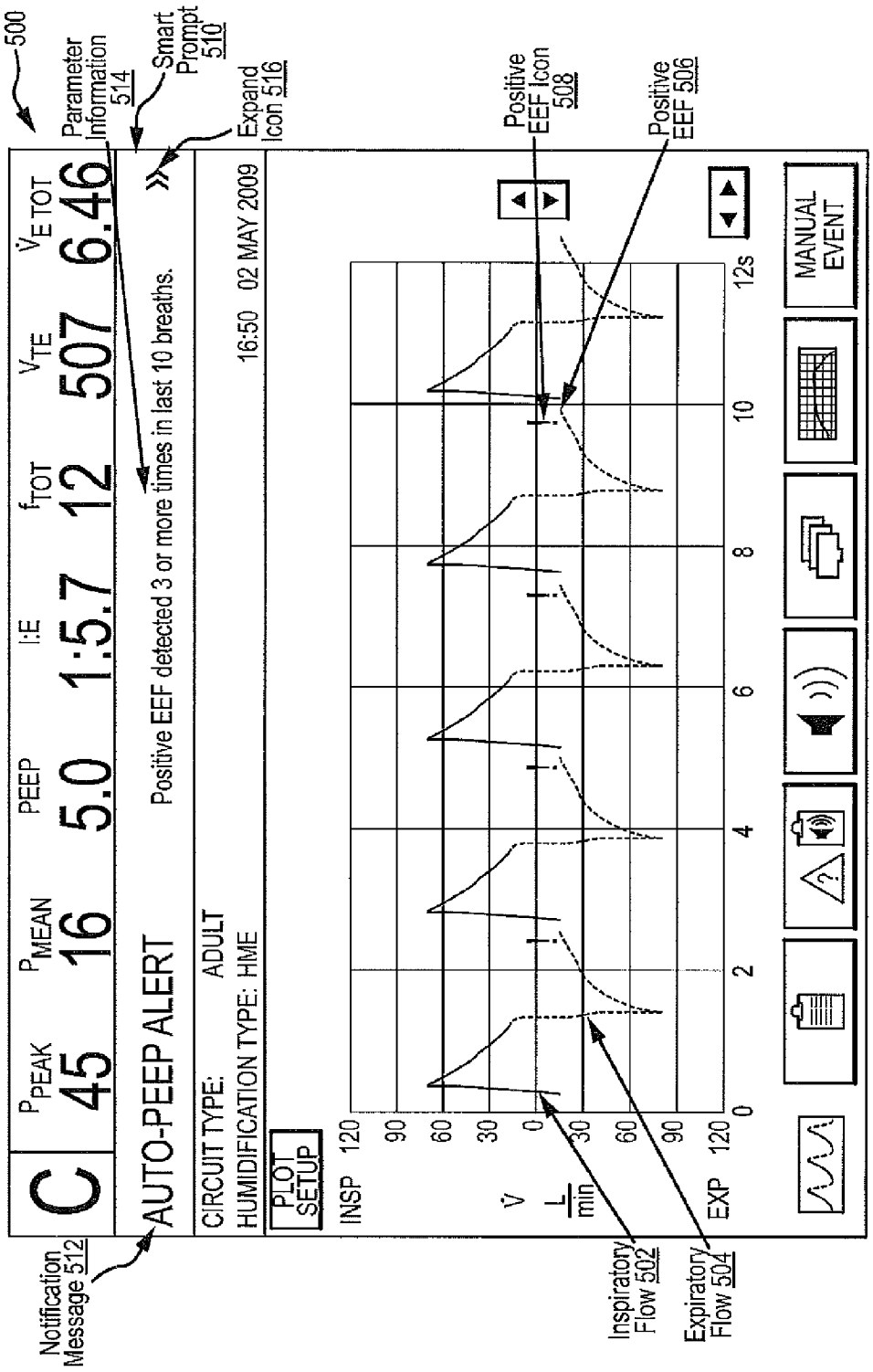
FIG. 5 is an illustration of an embodiment of a graphical user interface displaying a smart prompt having a notification message.

FIG. 5 is an illustration of an embodiment of a graphical user interface displaying a smart prompt having a notification message.

Graphical user interface 500 may display various monitored and/or derived data to the clinician during ventilation of a patient. In addition, graphical user interface 500 may display various messages to the clinician (e.g., alarm messages, etc.). Specifically, graphical user interface 500 may display a smart prompt as described herein.

According to embodiments, the ventilator may monitor and evaluate various ventilatory parameters based on one or more predetermined thresholds to detect Auto-PEEP. As illustrated, a flow waveform may be generated and displayed by the ventilator on graphical user interface 500. As further illustrated, the flow waveform may be displayed such that inspiratory flow 502 is represented in a different color (e.g., green) than expiratory flow 504 (e.g., yellow). Although expiratory flow may preferably approximate zero at the end of expiration, in some instances EEF may not reach zero before inspiration begins, as illustrated by positive EEF 506. According to further embodiments, positive EEF may be identified by a positive EEF icon 508, or other identifier, such that a clinician may readily identify positive EEF on the flow waveform. Additionally or alternatively, the flow waveform may be frozen for a period of time such that the clinician may be alerted as to the position in time of the incidence of positive EEF along the flow waveform. Additionally or alternatively, positive EEF icon 508 may also include an informative text message indicating that positive EEF was detected.

That is, positive EEF may be detected if EEF breaches a predetermined threshold associated with EEF (e.g., if EEF exceeds about 5 L/m). According to embodiments, when positive EEF is detected in a threshold number of breaths, e.g., three or more times in ten consecutive breaths, the ventilator may determine that Auto-PEEP is implicated. According to other embodiments, when resistance increases by a predetermined threshold (e.g., about 5 cm $H_2O/L/s$ or more), the ventilator may determine that Auto-PEEP is implicated. According to further embodiments, when compliance increases by a predetermined threshold (e.g., about 10 mL/cm $H_2O$ or more), the ventilator may determine that Auto-PEEP is implicated. According to further embodiments, e.g., when EEP exceeds PEEP by a threshold amount for a threshold number of breaths (e.g., about 5 cm $H_2O$ above set PEEP detected in three or more of ten consecutive breaths), the ventilator may determine that Auto-PEEP is implicated. Upon a determination that Auto-PEEP is implicated, the graphical user interface 500 may display a smart prompt, e.g., smart prompt 510.

According to embodiments, smart prompt 510 may be displayed in any suitable location such that a clinician may be alerted regarding a detected patient condition, but while allowing other ventilatory displays and data to be visualized substantially simultaneously. As illustrated, smart prompt 510 is presented as a bar or banner across an upper region of the graphical user interface 500. However, as previously noted, smart prompt 510 may be displayed as a tab, icon, button, banner, bar, or any other suitable shape or form. Further, smart prompt 510 may be displayed in any suitable location within the graphical user interface 500. For example, smart prompt 510 may be located along any border region of the graphical user interface 500 (e.g., top, bottom, or side borders) (not shown), across an upper region (shown), or in any other suitable location. Further, as described herein, smart prompt 510 may be partially transparent (not shown) such that ventilatory displays and data may be at least partially visible behind smart prompt 510.

Specifically, smart prompt 510 may alert the clinician that Auto-PEEP has been detected, for example by notification message 512. As described herein, notification message 512 may alert the clinician that Auto-PEEP is implicated via any suitable means, e.g., "Auto-PEEP Alert" (shown), "Auto-PEEP Detected" (not shown), or "Auto-PEEP Implicated" (not shown). Smart prompt 510 may further include information regarding ventilatory parameters that implicated Auto-PEEP. For example, if Auto-PEEP was detected based on a positive EEF over multiple breaths, this information may be provided to the clinician (e.g., "Positive EEF detected 3 or more times in last 10 breaths," shown). According to the illustrated embodiment, parameter information 514 is provided along with the notification message 512 in a banner. According to alternative embodiments, in addition to the notification message 512 and the parameter information 514, one or more recommendation messages may be provided in an initial smart prompt banner (not shown). According to other embodiments, rather than providing information regarding ventilatory parameters that implicated Auto-PEEP in the initial smart prompt, this information may be provided within an expanded portion (not shown) of smart prompt 510.

According to embodiments, smart prompt 510 may be expanded to provide additional information and/or recommendations to the clinician regarding a detected patient condition. For example, an expand icon 516 may be provided within a suitable area of the smart prompt 510. According to embodiments, upon selection of the expand icon 516 via any suitable means, the clinician may optionally expand the smart prompt 510 to acquire additional information and/or recommendations for mitigating the detected patient condition. According to further embodiments, smart prompt 510 may include links (not shown) to additional settings and/or display screens of the graphical user interface 500 such that the clinician may easily and quickly mitigate and/or verify the detected condition.

As may be appreciated, the disclosed data, graphics, and smart prompt illustrated in graphical user interface 500 may be arranged in any suitable order or configuration such that information and alerts may be communicated to the clinician in an efficient and orderly manner. The disclosed data, graphics, and smart prompt are not to be understood as an exclusive array, as any number of similar suitable elements may be displayed for the clinician within the spirit of the present disclosure. Further, the disclosed data, graphics, and smart prompt are not to be understood as a necessary array, as any number of the disclosed elements may be appropriately replaced by other suitable elements without departing from the spirit of the present disclosure. The illustrated embodiment of the graphical user interface 500 is provided as an example only, including potentially useful information and alerts that may be provided to the clinician to facilitate communication of detected Auto-PEEP in an orderly and informative way, as described herein.

Ventilator GUI Display of Expanded Smart Prompt

Figure 6:
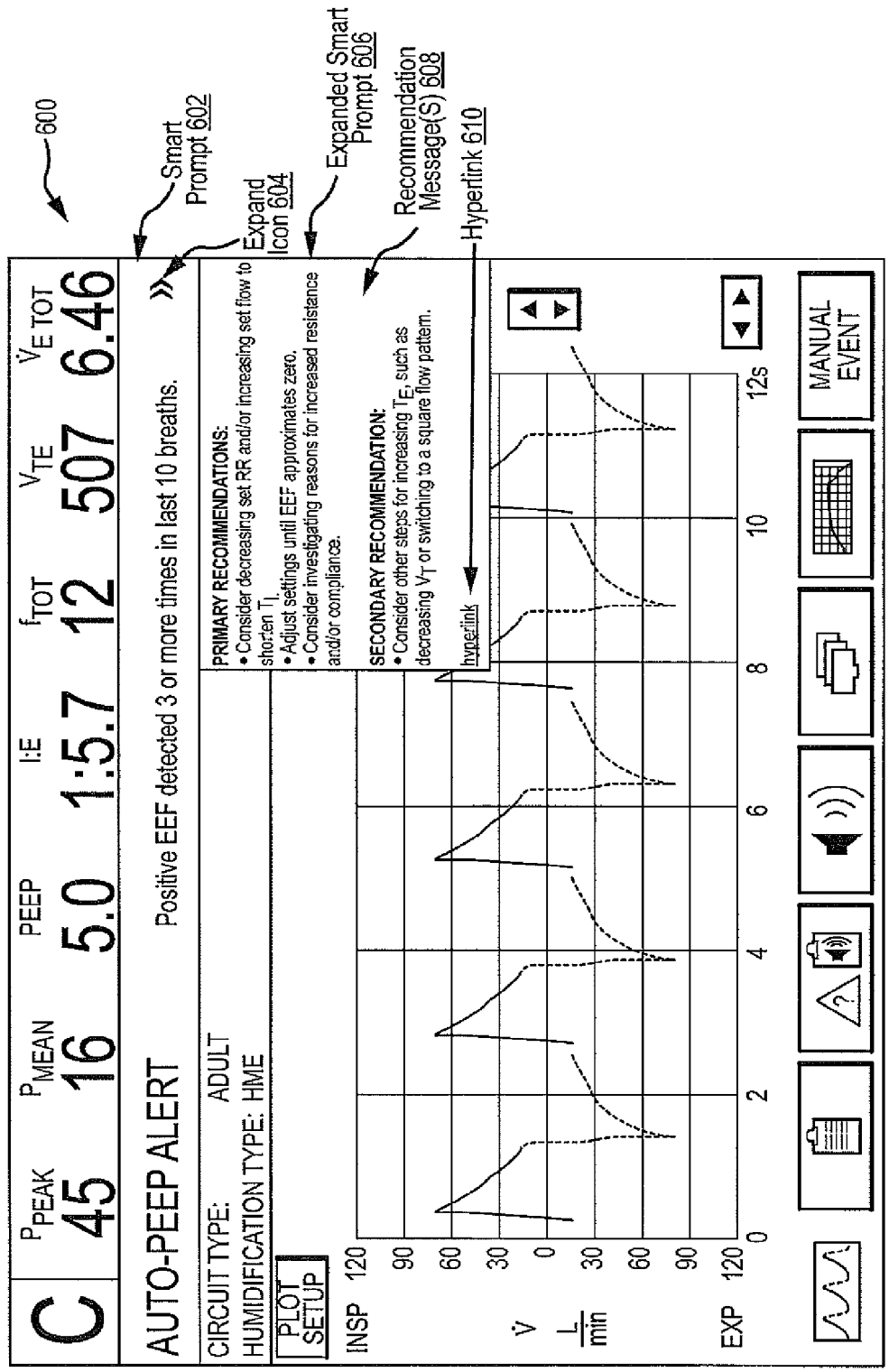
FIG. 6 is an illustration of an embodiment of a graphical user interface displaying an expanded smart prompt having a notification message and one or more recommendation messages.

FIG. 6 is an illustration of an embodiment of a graphical user interface displaying an expanded smart prompt having a notification message and one or more recommendation messages.

Graphical user interface 600 may display various monitored and/or derived data to the clinician during ventilation of a patient. In addition, graphical user interface 600 may display an expanded smart prompt including one or more recommendation messages as described herein.

According to embodiments, as described above, an expand icon 604 may be provided within a suitable area of smart prompt 602. Upon selection of the expand icon 604, the clinician may optionally expand smart prompt 602 to acquire additional information and/or recommendations for mitigating the detected patient condition. For example, expanded smart prompt 606 may be provided upon selection of expand icon 604. As described above for smart prompt 510, expanded smart prompt 606 may be displayed as a tab, icon, button, banner, bar, or any other suitable shape or form. Further, expanded smart prompt 606 may be displayed in any suitable location within the graphical user interface 600. For example, expanded smart prompt 606 may be displayed below (shown) smart prompt 602, to a side (not shown) of smart prompt 602, or otherwise logically associated with smart prompt 602. According to other embodiments, an initial smart prompt may be hidden (not shown) upon displaying expanded smart prompt 606. Expanded smart prompt 606 may also be partially transparent (not shown) such that ventilatory displays and data may be at least partially visible behind expanded smart prompt 606.

According to embodiments, expanded smart prompt 606 may comprise additional information (not shown) and/or one or more recommendation messages 608 regarding detected Auto-PEEP. For example, the one or more recommendation messages 608 may include a primary recommendation message and a secondary recommendation message. The primary recommendation message may provide one or more specific suggestions for mitigating Auto-PEEP during volume ventilation of a non-triggering patient. For example, if Auto-PEEP was implicated by positive EEF over several breaths, the one or more recommendation messages may include: "Consider increasing respiratory rate and/or set flow to shorten $T_I$; Adjust settings until EEF approximates zero; Investigate reasons for increased resistance and/or compliance." Alternately, if Auto-PEEP was implicated by increased resistance, the one or more recommendation messages may also include suctioning the patient interface, repositioning the patient, etc. The secondary recommendation message may provide one or more general suggestions for mitigating Auto-PEEP. For example, the secondary recommendation message may include: "Consider other steps for increasing $T_E$, such as decreasing $V_T$ or switching to a square flow waveform."

According to embodiments, expanded smart prompt 606 may also include one or more hyperlinks 610, which may provide immediate access to the display and/or settings screens associated with detected Auto-PEEP. For example, associated parameter settings screens may be accessed from expanded smart prompt 606 via hyperlink 610 such that the clinician may address detected Auto-PEEP by adjusting one or more parameter settings as necessary. Alternatively, associated parameter display screens may be accessed such that the clinician may view clinical data associated with Auto-PEEP in the form of charts, graphs, or otherwise. That is, according to embodiments, the clinician may access the ventilatory data that implicated Auto-PEEP for verification purposes. For example, when Auto-PEEP has been implicated, depending on the particular ventilatory parameters that implicated Auto-PEEP, the clinician may be able to access associated parameter settings screens for addressing Auto-PEEP (e.g., settings screens for adjusting $V_T$, $T_I$, RR, flow, etc.). Additionally or alternatively, the clinician may be able to access and/or view display screens associated with the ventilatory parameters that implicated Auto-PEEP (e.g., a graphics screen displaying historical flow waveforms, volume waveforms, and/or pressure waveforms that gave rise to implications of Auto-PEEP).

As may be appreciated, the disclosed smart prompt and recommendation messages illustrated in graphical user interface 600 may be arranged in any suitable order or configuration such that information and alerts may be communicated to the clinician in an efficient and orderly manner. Indeed, the illustrated embodiment of the graphical user interface 600 is provided as an example only, including potentially useful information and recommendations that may be provided to the clinician to facilitate communication of suggestions for mitigating detected Auto-PEEP in an orderly and informative way, as described herein.

Unless otherwise indicated, all numbers expressing measurements, dimensions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5, etc. This same principle applies to ranges reciting only one numerical value. Furthermore, such an interpretation should apply regardless of the breadth of the range or the characteristics being described.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A ventilator-implemented method for detecting Auto-PEEP during volume ventilation of a non-triggering patient, the method comprising:
   receiving one or more ventilatory settings associated with volume ventilation of the non-triggering patient;
   collecting data associated with ventilatory parameters;
   processing at least some of the collected ventilatory parameter data, wherein processing the collected ventilatory parameter data includes deriving ventilatory parameter data from at least some of the collected ventilatory parameter data;
   analyzing the processed ventilatory parameter data, wherein analyzing the processed ventilatory parameter data comprises:
      determining one or more predetermined thresholds for detecting Auto-PEEP based at least in part on the one or more ventilatory settings; and
      monitoring whether the processed ventilatory parameter data breaches the one or more predetermined thresholds;
   determining, by the ventilator, that Auto-PEEP is implicated for the non-triggering patient upon detecting that the processed ventilatory data breaches the one or more predetermined thresholds;
   determining a list of entries for mitigating Auto-PEEP based at least in part on identifying the patient as non-triggering; and
   issuing a smart prompt when Auto-PEEP is implicated, the smart prompt displaying:
      a notification that Auto-PEEP is implicated; and
      the list of entries for mitigating Auto-PEEP, comprising one or more of:
         decrease respiratory rate;
         increase flow;
         adjust ventilatory settings until end-expiratory flow (EEF) approximates zero;
         investigate reasons for increased resistance; and
         investigate reasons for increased compliance.

2. The method of claim 1, wherein the processed ventilatory parameter data includes expiratory flow data, and wherein analyzing the processed ventilatory parameter data further comprises:
   receiving one or more predetermined thresholds associated with end-expiratory flow (EEF);
   detecting that EEF is positive when the EEF breaches the one or more predetermined thresholds; and
   determining that Auto-PEEP is implicated for the non-triggering patient when EEF is positive for a predetermined number of breaths.

3. The method of claim 1, wherein the processed ventilatory parameter data includes respiratory resistance and respiratory compliance data, further comprising:
   calculating a time required to reach functional residual capacity (FRC);
   comparing the time required to reach FRC with expiratory time ($T_E$);
   determining that Auto-PEEP is implicated for the non-triggering patient when the time required to reach FRC is greater than $T_E$.

4. The method of claim 1, wherein the processed ventilatory parameter data includes pressure data, and wherein analyzing the processed ventilatory parameter data further comprises:
   receiving a positive end-expiratory pressure (PEEP) setting, wherein the PEEP setting is about 0 cm $H_2O$ or greater;
   receiving one or more predetermined thresholds associated with end-expiratory pressure (EEP);
   detecting that the EEP breaches the one or more predetermined thresholds when the EEP minus the PEEP setting is greater than the one or more predetermined thresholds; and
   determining that Auto-PEEP is implicated for the non-triggering patient when the EEP breaches the one or more predetermined thresholds.

5. The method of claim 1, wherein the processed ventilatory parameter data includes respiratory resistance data, and wherein analyzing the processed ventilatory parameter data further comprises:
   receiving one or more predetermined thresholds associated with the respiratory resistance data;
   detecting that respiratory resistance has increased when the respiratory resistance data breaches the one or more predetermined thresholds; and
   determining that Auto-PEEP is implicated for the non-triggering patient when the respiratory resistance has increased.

6. The method of claim 1, wherein the processed ventilatory parameter data includes a pulmonary time constant and an expiratory time ($T_E$), and wherein analyzing the processed ventilatory parameter data further comprises:
   comparing the pulmonary time constant to the $T_E$; and
   determining that Auto-PEEP is implicated for the non-triggering patient when the $T_E$ is less than three pulmonary time constants.

7. A ventilatory system for issuing a smart prompt when Auto-PEEP is implicated during volume ventilation of a non-triggering patient, comprising:
- at least one processor; and
- at least one memory, communicatively coupled to the at least one processor and containing instructions that, when executed by the at least one processor, cause a controller to issue a smart prompt, the controller comprising:
  - a user interface for receiving one or more ventilatory settings associated with volume ventilation of the non-triggering patient;
  - an Auto-PEEP detection module for detecting that Auto-PEEP is implicated for the non-triggering patient upon detecting that parameter data breaches one or more predetermined thresholds, wherein the one or more predetermined thresholds are based at least in part on the one or more ventilatory settings;
  - a smart prompt module for:
    - determining a list of entries for mitigating Auto-PEEP based at least in part on identifying the patient as non-triggering; and
    - issuing a smart prompt when Auto-PEEP is implicated, the smart prompt displaying:
      - a notification that Auto-PEEP is implicated; and
      - a list of entries for mitigating Auto-PEEP, the list of entries including one or more primary entries comprising one or more of:
        - decrease respiratory rate;
        - increase flow;
        - adjust ventilatory settings until end-expiratory flow (EEF) approximates zero;
        - investigate reasons for increased resistance; and
        - investigate reasons for increased compliance.

8. The ventilatory system of claim 7, further comprising: determining the notification based at least in part on the parameter data that implicated Auto-PEEP.

9. The ventilatory system of claim 8, wherein the notification comprises information regarding the parameter data that implicated Auto-PEEP.

10. The ventilatory system of claim 7, wherein the list of entries for mitigating Auto-PEEP are based at least in part on evaluating the parameter data that implicated Auto-PEEP.

11. The ventilatory system of claim 7, wherein the list of entries further includes one or more secondary entries.

12. The ventilatory system of claim 11, wherein the secondary entries include increasing expiratory time ($T_E$) by one or more of:
- decreasing tidal volume ($V_T$); and
- changing to a square flow waveform.

13. A ventilator-implemented method for detecting Auto-PEEP during volume ventilation of a non-triggering patient, the method comprising:
- collecting data associated with ventilatory parameters;
- determining one or more predetermined thresholds for detecting Auto-PEEP; and
- determining, by the ventilator, that Auto-PEEP is implicated for the non-triggering patient upon detecting that the processed ventilatory data breaches the one or more predetermined thresholds;
- determining a list of entries for mitigating Auto-PEEP based at least in part on identifying the patient as non-triggering; and
- issuing a smart prompt when Auto-PEEP is implicated, the smart prompt displaying:
  - a notification that Auto-PEEP is implicated; and
  - the list of entries for mitigating Auto-PEEP.

14. The method of claim 13, wherein the ventilatory parameter data includes expiratory flow data, the method further comprising:
- receiving one or more predetermined thresholds associated with end-expiratory flow (EEF);
- detecting that EEF is positive when the EEF breaches the one or more predetermined thresholds; and
- determining that Auto-PEEP is implicated for the non-triggering patient when EEF is positive for a predetermined number of breaths.

15. The method of claim 13, wherein the ventilatory parameter data includes respiratory resistance data and respiratory compliance data, the method further comprising:
- calculating a time required to reach functional residual capacity (FRC);
- comparing the time required to reach FRC with expiratory time ($T_E$);
- determining that Auto-PEEP is implicated for the non-triggering patient when the time required to reach FRC is greater than $T_E$.

16. The method of claim 13, wherein the ventilatory parameter data includes pressure data, and wherein analyzing the processed ventilatory parameter data further comprises:
- receiving a positive end-expiratory pressure (PEEP) setting, wherein the PEEP setting is about 0 cm $H_2O$ or greater;
- receiving one or more predetermined thresholds associated with end-expiratory pressure (EEP);
- detecting that the EEP breaches the one or more predetermined thresholds when the EEP minus the PEEP setting is greater than the one or more predetermined thresholds; and
- determining that Auto-PEEP is implicated for the non-triggering patient when the EEP breaches the one or more predetermined thresholds.

17. The method of claim 13, wherein the ventilatory parameter data includes respiratory resistance data, the method further comprising:
- receiving one or more predetermined thresholds associated with the respiratory resistance data;
- detecting that respiratory resistance has increased when the respiratory resistance data breaches the one or more predetermined thresholds; and
- determining that Auto-PEEP is implicated for the non-triggering patient when the respiratory resistance has increased.

18. The method of claim 13, wherein the ventilatory parameter data includes a pulmonary time constant and an expiratory time ($T_E$), the method further comprising:
- comparing the pulmonary time constant to the $T_E$; and
- determining that Auto-PEEP is implicated for the non-triggering patient when the $T_E$ is less than three pulmonary time constants.

* * * * *